US009365548B2

(12) United States Patent
Edwards et al.

(10) Patent No.: US 9,365,548 B2
(45) Date of Patent: *Jun. 14, 2016

(54) BENZOIMIDAZOL-2-YL PYRIMIDINES AND PYRAZINES AS MODULATORS OF THE HISTAMINE H4 RECEPTOR

(71) Applicant: Janssen Pharmaceutica NV, Beerse (BE)

(72) Inventors: James P. Edwards, San Diego, CA (US); David E. Kindrachuk, Cardiff by the Sea, CA (US); Christopher M. Mapes, La Jolla, CA (US); Daniel J. Pippel, Del Mar, CA (US); Jennifer D. Venable, Solana Beach, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/607,946

(22) Filed: Jan. 28, 2015

(65) Prior Publication Data

US 2015/0148361 A1 May 28, 2015

Related U.S. Application Data

(63) Continuation of application No. 14/051,962, filed on Oct. 11, 2013, now Pat. No. 8,962,644, which is a continuation of application No. 13/676,595, filed on Nov. 14, 2012, now Pat. No. 8,598,189, which is a continuation of application No. 12/816,995, filed on Jun. 16, 2010, now Pat. No. 8,343,989, which is a continuation of application No. 12/321,208, filed on Jan. 15, 2009, now abandoned, which is a continuation of application No. 11/731,074, filed on Mar. 30, 2007, now Pat. No. 7,507,737.

(60) Provisional application No. 60/788,190, filed on Mar. 31, 2006.

(51) Int. Cl.
*C07D 401/14* (2006.01)
*A61K 31/4184* (2006.01)
*C07D 403/14* (2006.01)

(52) U.S. Cl.
CPC ............ *C07D 401/14* (2013.01); *C07D 403/14* (2013.01); *A61K 31/4184* (2013.01)

(58) Field of Classification Search
CPC ............................ C07D 401/14; A61K 31/506
USPC ........................................... 544/331; 514/275
See application file for complete search history.

(56) References Cited

U.S. PATENT DOCUMENTS

| 3,005,852 A | 10/1961 | Freyermuth |
| 3,609,152 A | 9/1971 | Hess |
| 3,931,195 A | 1/1976 | Dykstra |
| 4,190,601 A | 2/1980 | Decker |
| 4,191,828 A | 3/1980 | Horgan |
| 4,337,341 A | 6/1982 | Zimmerman |
| 5,614,524 A | 3/1997 | Matassa et al. |
| 5,621,097 A | 4/1997 | Brown |
| 5,880,140 A | 3/1999 | Anthony |
| 5,883,105 A | 3/1999 | Anthony |
| 5,939,439 A | 8/1999 | Anthony et al. |
| 5,945,422 A | 8/1999 | Doherty |
| 6,051,574 A | 4/2000 | Anthony |
| 6,077,853 A | 6/2000 | Graham et al. |
| 6,210,394 B1 | 4/2001 | Demopulos et al. |
| 6,242,460 B1 | 6/2001 | Ettema |
| 6,372,743 B1 | 4/2002 | Darrow |
| 6,624,180 B2 | 9/2003 | South et al. |
| 6,693,194 B2 | 2/2004 | Jau |
| 6,828,338 B2 | 12/2004 | South et al. |
| 6,835,726 B2 | 12/2004 | Cushing |
| 6,858,600 B2 | 2/2005 | Hamilton et al. |
| 6,916,938 B2 | 7/2005 | Oguma |
| 6,989,383 B1 | 1/2006 | Rosen et al. |
| 7,148,236 B2 | 12/2006 | Astles et al. |
| 7,250,427 B2 | 7/2007 | Breitenbucher et al. |
| 7,312,246 B2 | 12/2007 | Hamilton et al. |
| 7,314,937 B2 | 1/2008 | Beavers et al. |
| 7,405,221 B2 | 7/2008 | Kopka et al. |
| 7,507,737 B2 | 3/2009 | Edwards et al. |
| 7,576,092 B2 | 8/2009 | Chavez |
| 7,923,451 B2 | 4/2011 | Edwards et al. |
| 7,928,131 B2 | 4/2011 | Buzard et al. |
| 8,084,466 B2 | 12/2011 | Kindrachuk et al. |
| 8,309,709 B2 | 11/2012 | Berg et al. |
| 8,309,720 B2 | 11/2012 | Cesco-Cancian |

(Continued)

FOREIGN PATENT DOCUMENTS

| CN | 101032483 A | 9/2007 |
| JP | S59 42396 A | 3/1984 |

(Continued)

OTHER PUBLICATIONS

Amin et al. "Inflammation and Structural Changes in the Airways of Patients with Atopic and NonAtopic Asthma" Am J Resp. Crit Care Med 2000 vol. 162(6) pp. 2295-2301.
Altenbach, R. et al. Structure-Activity Studies on a Series of a 2-Aminopyrimidine-Containing Histamine H4 Receptor Ligands. Jour. Med. Chem. 2008. vol. 51(20), 6571-6580.
Bagshawe et al. "Antibody-Directed Enzyme Prodrug Therapy: A Review" Drug Dev Res 1995 vol. 34 pp. 220-230.
Bell et al "Involvement of Histamine $H_4$ and $H_1$ Receptors in Scratching Induced by Histamine Receptor Agonists in BalbC Mice" Br J Pharmaol 2004 vol. 142(2) pp. 374-380.
Benoist et al "Mast Cells in Autoimmune Disease" Nature 2002 vol. 420(6917) pp. 875-878.

(Continued)

Primary Examiner — Deepak Rao

(57) ABSTRACT

Benzoimidazol-2-yl pyrimidines and pyrazines, pharmaceutical compositions and methods for the treatment of disease states, disorders, and conditions mediated by $H_4$ receptor activity, including allergy, asthma, autoimmune diseases, and pruritis.

2 Claims, No Drawings

(56) References Cited

U.S. PATENT DOCUMENTS

| | | | |
|---|---|---|---|
| 8,343,989 B2 | 1/2013 | Edwards et al. | |
| 8,598,189 B2 | 12/2013 | Edwards et al. | |
| 8,841,287 B2 | 9/2014 | Cai et al. | |
| 8,859,575 B2 | 10/2014 | Conza et al. | |
| 8,962,644 B2 * | 2/2015 | Edwards et al. | 514/275 |
| 2002/0077332 A1 | 6/2002 | Aronhime | |
| 2003/0187026 A1 | 10/2003 | Li et al. | |
| 2003/0207893 A1 | 11/2003 | Carruthers et al. | |
| 2004/0048878 A1 | 3/2004 | Cui et al. | |
| 2004/0058934 A1 | 3/2004 | Carruthers et al. | |
| 2004/0105856 A1 | 6/2004 | Thurmond et al. | |
| 2004/0127395 A1 | 7/2004 | Desai | |
| 2004/0132715 A1 | 7/2004 | Dunford et al. | |
| 2004/0224964 A1 | 11/2004 | O'Yang | |
| 2004/0261190 A1 | 12/2004 | Eggenweiler | |
| 2005/0070527 A1 | 3/2005 | Edwards et al. | |
| 2005/0070550 A1 | 3/2005 | Arienti et al. | |
| 2005/0181023 A1 | 8/2005 | Young et al. | |
| 2005/0261309 A1 | 11/2005 | Buzard et al. | |
| 2006/0089496 A1 | 4/2006 | Lam et al. | |
| 2006/0281712 A1 | 12/2006 | Yen et al. | |
| 2007/0043043 A1 | 2/2007 | Chen et al. | |
| 2007/0099938 A1 | 5/2007 | Ohmoto et al. | |
| 2007/0185163 A1 | 8/2007 | Hunt | |
| 2007/0232616 A1 | 10/2007 | Edwards et al. | |
| 2007/0238771 A1 | 10/2007 | Edwards et al. | |
| 2007/0244126 A1 | 10/2007 | Edwards et al. | |
| 2007/0265250 A1 | 11/2007 | Buzard et al. | |
| 2008/0015200 A1 | 1/2008 | Chavez et al. | |
| 2008/0119494 A1 | 5/2008 | Young et al. | |
| 2008/0132513 A1 | 6/2008 | Che | |
| 2008/0194577 A1 | 8/2008 | Cai et al. | |
| 2008/0267887 A1 | 10/2008 | Yuan et al. | |
| 2009/0137608 A1 | 5/2009 | Edwards et al. | |
| 2009/0143302 A1 | 6/2009 | Yen et al. | |
| 2009/0182142 A1 | 7/2009 | Furukubo et al. | |
| 2010/0029942 A1 | 2/2010 | Cesco-Cancian et al. | |
| 2011/0076324 A1 | 3/2011 | Thurmond | |
| 2011/0184016 A1 | 7/2011 | Lerner | |
| 2012/0178932 A1 | 7/2012 | Cesco-Cancian et al. | |
| 2012/0184740 A1 | 7/2012 | Cesco-Cancian et al. | |
| 2013/0053561 A1 | 2/2013 | Cesco-Cancian | |
| 2013/0202685 A1 | 8/2013 | Thurmond | |
| 2013/0225816 A1 | 8/2013 | Cesco-Cancian | |
| 2014/0066624 A1 | 3/2014 | Cesco-Cancian | |
| 2014/0073795 A1 | 3/2014 | Cesco-Cancian | |
| 2014/0121374 A1 | 5/2014 | Cesco-Cancian | |

FOREIGN PATENT DOCUMENTS

| | | |
|---|---|---|
| JP | 61030576 A | 2/1986 |
| JP | 1996-502486 | 4/1994 |
| JP | 2003-502406 | 12/2000 |
| WO | WO 97/36890 | 10/1997 |
| WO | WO 97/36898 | 10/1997 |
| WO | WO 98 31359 | 7/1998 |
| WO | WO 98/44797 | 10/1998 |
| WO | WO 99 18079 | 4/1999 |
| WO | WO 99/41253 | 8/1999 |
| WO | WO 99 65897 | 12/1999 |
| WO | WO 01 00610 | 1/2001 |
| WO | WO 01/14376 | 3/2001 |
| WO | WO 01 47883 | 5/2001 |
| WO | WO 01/58871 | 8/2001 |
| WO | WO 02 00647 | 1/2002 |
| WO | WO 02 20495 | 3/2002 |
| WO | WO 02/064096 | 8/2002 |
| WO | WO 02/072548 A2 | 9/2002 |
| WO | WO 02 076438 | 10/2002 |
| WO | WO 02/076438 A2 | 10/2002 |
| WO | WO 02/078701 | 10/2002 |
| WO | WO 03 000254 | 3/2003 |
| WO | WO 03 051366 | 6/2003 |
| WO | WO 2004 012736 | 2/2004 |
| WO | WO 2004/012736 A1 | 2/2004 |
| WO | WO 2004 030625 | 4/2004 |
| WO | WO 2004/050610 | 6/2004 |
| WO | WO 2004/110350 | 12/2004 |
| WO | WO 2004 110350 | 12/2004 |
| WO | WO 2005/014579 | 2/2005 |
| WO | WO 2005 032490 | 4/2005 |
| WO | WO 2005/040135 | 4/2005 |
| WO | WO 2005 039485 | 5/2005 |
| WO | WO 2005 044807 | 5/2005 |
| WO | WO 2005/092066 | 10/2005 |
| WO | WO 2005/115993 | 11/2005 |
| WO | WO 2006/025567 | 3/2006 |
| WO | WO 2006/063466 | 6/2006 |
| WO | WO 2006/102645 | 9/2006 |
| WO | WO 2006/138304 | 12/2006 |
| WO | WO 2007/003604 | 1/2007 |
| WO | WO 2007 003604 | 1/2007 |
| WO | WO 2007/003604 A2 | 1/2007 |
| WO | WO 2007/031529 | 3/2007 |
| WO | WO 2007/044085 | 4/2007 |
| WO | WO 2007/059610 | 5/2007 |
| WO | WO 2007 070173 | 6/2007 |
| WO | WO 2007/092095 | 8/2007 |
| WO | WO 2007/095753 | 8/2007 |
| WO | WO 2007 117399 | 10/2007 |
| WO | WO 2007/117400 | 10/2007 |
| WO | WO 2007/117401 | 10/2007 |
| WO | WO 2007 120690 | 10/2007 |
| WO | WO 2007/124589 | 11/2007 |
| WO | WO 2007/134434 | 11/2007 |
| WO | WO 2009 068512 | 6/2009 |
| WO | WO 2009/152287 | 12/2009 |
| WO | WO 2010/002774 | 1/2010 |
| WO | WO 2010/002777 | 1/2010 |
| WO | WO 2012/060590 | 5/2012 |
| WO | WO 2012/069442 | 5/2012 |

OTHER PUBLICATIONS

Berge et al. "Pharmaceutical Salts" Journal of Pharmaceutical Sciences 1977 vol. 66(1) pp. 1-19.

Bertolini et al. "A New Rational Hypothesis for the Pharmacophore of the Active Metabolite of Leflunomide, A Potent Immunosuppressive Drug" J Med Chem 1997 vol. 40 pp. 2011-2016.

Bodor et al. "Novel Approaches to the Design of Safer Drugs: Soft Drugs and Site-Specific Chemical Delivery Systems" Advances in Drug Research 1984 vol. 13 pp. 224-331.

Bundgaard "Design of Prodrugs" 1985 Ed. Hans Bundgaard p. 1.

Cheng et al. "Relationship Between the Inhibition Constant ($K_1$) and the Concentration of Inhibitor Which Causes 50 Percent Inhibition ($I_{50}$) of an Enzymatic Reaction" Biochem Pharmacol 1973 vol. 22 pp. 3099-3108.

Coge et al "Structure and Expression of the Human Histamine $H_4$—Receptor Gene" Biochem Biophys Res Commun 2001 vol. 284(2) pp. 301-309.

Cohen J. "The Immunopathogenesis of Sepsis" Nature 2002 vol. 420(6917) pp. 885-891.

Coussens et al "Inflammation and Cancer" Nature 2002 vol. 420(6917) pp. 860-867.

Crimi et al "Increased Numbers of Mast Cells in Bronchial Mucosa After the Late Phase Asthmatic Response to Allergen" Am Rev Respir Dis 1991 vol. 144(6) pp. 1282-1286.

de Esch et al. "The Histamine $H_4$ Receptor as a New Therapeutic Target for Inflammation" Trends Pharmacol Sci 2005 vol. 26(9) pp. 462-469.

Dunford, P.J. et al. The histamine H4 receptor mediates allergic airway inflammation by regulating the activation of CD4+ T cells. Journal of Immunology, 2006. vol. 176(11), 7062-7070.

Dunford, P.J. et al. Histamine H4 receptor antagonists are superior to traditional antihistamines in the attenuation of experimental pruritus. J. Allergy Clin. Immunol. 2007, vol. 119(1), 176-183.

Fleisher et al. "Improved Oral Delivery: Solubility Limitations Overcome by the Use of Prodrugs" Advanced Drug Delivery Review 1996 vol. 19 pp. 115-130.

Fokkens et al "Dynamics of Mast Cells in the Nasal Mucosa of Patients with Allergic Rhinitis and Non-Allergic Controls: A Biopsy Study" Clin Exp Allergy 1992 vol. 22(7) pp. 701-710.

(56) References Cited

OTHER PUBLICATIONS

Fung-Leung et al. "Histamine $H_4$ Receptor Antagonists: The New Antihistamines?" Curr Opin Invest Drugs 2004 Voluem 5(11) pp. 1174-1183.
Gantner et al. "Histamines $H_4$ and $H_2$ Receptors Control Histamine-Induced Interleukin-16 Release from Human CD8+ T Cells" J Pharmacol Exp 2002 vol. 303(1) pp. 300-307.
Gauvreau et al "Increased Numbers of Both Airway Basophils and Mast Cells in Sputum after Allergen Inhalation Challenge of Atopic Asthmatics" Am J Resp Crit Care Med 2002 vol. 161(5) pp. 1473-1478.
Gutzmer et al "Histamine $H^4$ Receptor Stimulation Suppresses IL-12p70 Production and Mediates Chemotaxis in Human Monocyte-Derived Dendritic Cells" J Immunol 2005 vol. 174(9) pp. 5224-5232.
Hofstra et al "Histamine $H^4$ Receptor Mediates Chemotaxis and Calcium Mobilization of Mast Cells" J Pharmacol Exp Ther 2003 vol. 305(3) pp. 1212-1221.
Horr et al. STAT1 phosphorylation and cleavage is regulated by the histamine (H4) receptor in human atopic and non-atopic lymphocytes. International Immunopharmacology 2006, vol. 6 (10), 1577-1585.
Ikawa et al "Histamine $H^4$ Receptor Expression in Human Synovial Cells Obtained from Patients Suffering from Rheumatoid Arthristis" Biol Pharm Bull 2005 vol. 28(10) pp. 2016-2018.
Jablonowski, J. et al., The first potent and selective non-imidazole human histamine H4 receptor antagonists. Journal of Medicinal Chemistry, 2003. vol. 46(19), 3957-3960.
Jiang et al. Cloning and pharmacological characterization of the dog histamine H-4 receptor. European Journal of Pharmacology, 2008. vol. 592(1-3), 26-32.
Jokuti et al. Histamine H4 receptor expression is elevated in human nasal polyp tissue, Cell Biology International. 2007 vol. 31(11) 1367-1370.
Kassel et al. "Local Increase in the Number of Mast Cells and Expression of Nerve Growth Factor in the Bronchus of Asthmatic Patients after Repeated Inhalation of Allergen Low-Dose" Clin Exp Allergy 2001 vol. 31(9) pp. 1432-1440.
Kirby et al "Bronchoalveolar Cell Profiles of Asthmatic and NonAsthmatic Subjects" Am. Rev. Respir. Dis. 1987, vol. 136(2) pp. 379-383.
Kiss, R. et al. Histamine H4 receptor ligands and their potential therapeutic applications. Expert Opin. Ther. Patents, 2009, vol. 19(2), 119-135.
Robert Kiss & Gyorgy M. Keseru, "Novel Histamine H4 Receptor Ligands and Their Potential Therapeutic Applications: An Update", Research Centre for Natural Sciences, Hungarian Academy of Sciences, vol. 24, No. 11, 2014, pp. 1185-1197.
Krug et al "Interleukin 16 and T-cell Chemoattractant Activity in Bronchoalveolar Lavage 24 Hours After Allergen Challenge in Asthma" Am J Resp Crit Care Med 2000 vol. 162(1) pp. 105-111.
Lee-Dutra, A. et al., Identification of 2-arylbenzimidazoles as potent human histamine H-4 receptor ligands, Bioorganic & Medicinal Chemistry Letters 2006. vol. 16(23), 6043-6048.
Leite-de-Moraes, Cutting edge: histamine receptor H4 activation positively regulates in vivo IL-4 and IFN-gamma production by invariant NKT cells. Journal of Immunology, 2009. 182(3):1233-1236.
Libby P. "Inflammation in Atherosclerosis" Nature 2002 vol. 420 pp. 868-874.
Lim, H. et al., Evaluation of histamine H-1-, H-2-, and H-3-receptor ligands at the human histamine H-4 receptor: Identification of 4-methylhistamine as the first potent and selective H-4 receptor agonist. Journal of Pharmacology & Experimental Therapeutics, 2005, vol. 314(3), 1310-1321.
Ling et al. "Histamine $H^4$ Receptor Mediates Eosiniphil Chemolaxis with Cell Shape Change and Adhesion Molecule Upregulation" Br J. Pharmacol 2004 vol. 142(1) pp. 161-171.
Lippert et al "Human Skin Cells Express H2 and H4, but not H3 Receptors" J Invest Dermatol 2004 vol. 123(1) pp. 116-123.

Liu et al "Cloning of Pharmacological Characterization of a Fourth Histamine Receptor ($H^4$) Expressed in Bone Marro" Mol Pharmacol 2001 vol. 59(3) pp. 420-426.
Mashikian et al "Identification of IL-16 as the Lymphocyte Chemotactic Activity in the Bronchoalveolar Lavage Fluid of Histamine-Challenged Asthmatic Patients" J Allergy Clin Immunol 1998 vol. 101(6 Part 1) pp. 786-792.
Morse et al "Cloning and Characterization of Novel Human Histamine Receptor" J Pharmacol Exp. Ther 2001 vol. 296(3) pp. 1058-1066.
Nathan C. "Points of Control in Inflammation" Nature 2002 vol. 420(6917) pp. 846-852.
O'Reilly et al "Identification of $H^4$ Receptor in Human Eosinophilis—Role in Eosinophil Chemotaxis" J Recept Signal Transduction 2002 vol. 22(1-4) pp. 431-448.
Parsons et al. "Histamine and Its Receptors" British Jurnal of Pharmacology 2006 vol. 147 pp. S127-S-135.
Robinson et al "Discovery of the Hemifumarate and ($\alpha$-L-Alanyloxy)methyl Ester as Prodrugs of an Antirheumatic Oxindole: Prodrugs for the Enolic OH Group" J Med Chem 1996 vol. 39 pp. 10-18.
Robinson Malcom"Medical Therapy of Inflammatory Bowel Disease for the $21^{st}$ Century" Eur J. Surg 1998 Suppl 582 pp. 90-98.
Shan et al. "Prodrug Strategies Based on Intramolecular Cyclization Reactions" Journal of Pharmaceutical Sciences 1997 vol. 86(7) pp. 765-767.
Shultz, et al. "New Catalysts for the Oxidation of Sulfides to Sulfones with Hydrogen Peroxide" J. Org. Chem., 1963, 28, 1140.
Silverman Richard B. "Prodrugs and Drug Delivery Systems" The Organic Chemistry of Drug Design and Drug Action 1997 Chapter 8 pp. 353-399.
Singh et al. "Immune Therapy in Inflammation Bowel Disease and Models Colitis" British Journal of Surgery 2001 vol. 88 pp. 1558-1569.
Slater et al "Increase in epithelial Mast Cell Numbers in the Nasal Mucosa of Patients with Perennial Allergic Rhinitis" J Laryngol Otol 1996 vol. 110 pp. 929-933.
Smits, R.A. et al. Major advances in the development of histamine H4 receptor ligands. Drug Discovery Today, 2009, vol. 14(15-16):745-753.
Stark, H. (editor), Histamine H4 Receptor: A Novel Drug Target for Immunoregulation and Inflammation. Walter de Gruyter & Co (Dec. 2, 2013), Chapter 2,, Schreeb, A. et al., Histamine H4 Receptor Ligands.
Steinberg D. "Atherogenesis in Perspective: Hypercholesterolemia and Inflammation as Partners in Crime" Nature Med 2002 vol. 8(11) pp. 1211-1217.
Takeshita et al "Critical Role of Histamine $H_4$ Receptor in Leukotriene $B_4$ Production and Mast-Cell Dependent Neutrophil Recruitment Induced by Zymosan in Vivo" J Pharmacol Exp Ther 2003 vol. 307(3) pp. 1072-1078.
Terzioglu et al. "Synthesis and Structure-Activity Relationship of Indole and Benzimidazole Piperazines as Histamine $H_4$ Receptor Antagonists" Bioorg & Med Chemistry Letters 2004 vol. 14 pp. 5251-5256.
Testa et al "Predicting Drug Metabolism: Concepts and Challenges" Pure Appl Chem 2004 vol. 76(5) pp. 907-914.
Thurmond R. L. et al , The role of histamine H1 and H4 receptors in allergic inflammation: the search for new antihistamines. Nat. Rev. Drug Disc. 2008 vol. 7(1), 45-53.
Tracey K. J. "The Inflammatory Reflex" Nature 2002 vol. 420(6917) pp. 853-859.
Ulrich, J and Stelzer, T. (2001) Kirk-Othmer Encyclopedia of Chemical Technology, "Crystallization", 1-63.
Varga et al "Inhibitory Effects of Histamine $H^4$ Receptor Antagonists on Experimental Colitis in the Rat" Eur J Pharmacol 2005 vol. 522(1-3) pp. 130-138.
Venable, J.D. et al. Preparation and biological evaluation of indole, benzimidazole, and thienopyrrole piperazine carboxamides: Potent human histamine $H_4$ antagonists. Journal of Medicinal Chemistry, 2005. vol. 48(26), 8289-8298.

(56) References Cited

OTHER PUBLICATIONS

Voehringer et al "Type 2 Immunity Reflects Orchestrated Recruitment of Cells Committed to IL-4 Production" Immunity 2004 vol. 20(3) pp. 267-277.
Weiner et al "Inflammation and Therapeutic Vaccination in CNS Diseases" Nature 2002 vol. 420(6917) pp. 879-884.
Zhang, M. et al. The histamine $H_4$ receptor in autoimmune disease. Expert Opinion on Investigational Drugs, 2006. vol. 15(11), 1443-1452.
Zhang, M. et al. The Histamine H4 Receptor: A Novel Mediator of Inflammatory and Immune Disorders. Pharmacol. Ther. 2007. vol. 113, 594-606.
Zhichkin et al. "A General Procedure for the Synthesis of 2-Substituted Pyrimidine-5-Carboxylic Esters" Synthesis 2002 vol. 6 pp. 720-722.
International Search Report and Written Opinion for WO2014/138368, Jun. 6, 2014.
U.S. Appl. No. 60/971,676, filed Sep. 12, 2007, Gual et al.
U.S. Appl. No. 60/972,589, filed Sep. 14, 2007, Edwards.
U.S. Appl. No. 61/014,572, filed Oct. 18, 2007, Kindrachuk.
Abarghaz, M. et al., "Regioselective Alkylation of the Exocyclic Nitrogen of Heterocyclic Amides via the Mitsunobu Reaction", Tetrahedron Letters, 1995, vol. 36, pp. 6463-6466.
Adachi, S. et al., "The Prevention of Postoperative Intraperitoneal Adhesions by Tranilast: N-(3',4'-dimethoxycinnamoyl) Anthranilic Acid", Surgery Today, Jpn J. Surg. (1999) 29:51-54.
Avsar, A.F. et al., "Dyphenhydramine and hyaluronic acid derivatives reduce adnexal adhesions and prevent tubal obstructions in rats", European Journal of Obstetrics & Gynecology and Reproductive Biology 2003, vol. 106, pp. 50-54.
Bäumer, Wolfgang, et al., International Symposium on Atopic Dermatitis, Munich, Germany "Lack of preventing effect of systemically and topically administered histamine $H_4$ receptor antagonists in a canine model of atopic dermatitis" Jul. 22, 2010.
Bäumer, W., et al., "Histamine H1 and H4 Receptor Antagonists Do Not Prevent Acute Skin Lesions in a Canine Model of Atopic Dermatitis", European Histamine Research Society Meeting Sochi, Russia May 12, 2011, Oral Presentation.
Baumer, W., et. al., "Lack of preventing effect of systemically and topically administered histamine H1 or H4 receptor antagonists in a dog model of acute atopic dermatitis", Experimental Dermatology, 2011, pp. 1-5.
Bhatt, H. G. et al., "Histamine H4 Receptor: A Novel Therapeutic Target for Immune and Allergic Responses", Mini-Reviews in Medicinal Chemistry, 2010, 10, 1293-1308.
Brown, et al.,Journal of the Chemical Society [Section C], Organic, 1967, (19), 1928-1933.
Buckland et al "Histamine Induces Cytoskeletal Changes in Human Eosinophils via the $H_4$ Receptor" Br J Pharmacol 2003 vol. 140(6) pp. 1117-1127.
www.clinicaltrials.gov, "A Phase 2b Randomized, Double-blind, Placebo-controlled, Parallel Group, Dose Range Finding Study of JNJ-38518168 in Subjects with Active Rheumatoid Arthritis Despite Concomitant Methotrexate therapy", downloaded Jul. 23, 2014.
www.clinicaltrials.gov, "A Phase 2a Randomized, Double-blind, Placebo-controlled, Multicenter, Parallel Group Study of JNJ-38518168 in Adult Subjects with Uncontrolled, Persistent Asthma", downloaded Jul. 23, 2014.
Cowden, J. M.; et al., The Histamine H4 Receptor Mediates Inflammation in Th2-dependent Dermal Inflammation European Histamine Research Society Meeting, Fulda, Germany May 14, 2009.
Cowden, J.M. et al., "Antagonism of the Histamine $H_4$ Receptor Reduces LPS-induced TNF Production In Vivo", European Histamine Research Society Meeting, Belfast, UK May 4, 2012.
Cowden, J.M. et al., "The Histamine $H_4$ Receptor Mediates Inflammation in Models of Arthritis via Inhibition of Th17", International Congress of Immunology, Milan, Italy Aug. 27, 2013.
Cowden, J. M., et al., "The Histamine H4 Receptor Mediates Inflammation and Pruritus in Th2-Dependent Dermal Inflammation", Journal of Investigative Dermatology (2010) 130, 1023-1033.
Cowden, J. M., et al., Antagonism of the histamine H4 receptor reduces LPS-induced TNF production in vivo, Inflamm. Res. (2013) 62:599-607.
Cowden, J. M., et al., "The histamine H4 receptor mediates inflammation and Th17 responses in preclinical models of arthritis", Ann Rheum Dis 2014;73:600-608.
Desai, P. and Thurmond, R. L., "Histamine H4 receptor activation enhances LPS-induced IL-6 production in mast cells via ERK and PI3K activation", Eur. J. Immunol. 2011. 41: 1764-1773.
Dibb, Karin, et al., "The histamine H4 receptor is a potent inhibitor of adhesion-dependent degranulation in human neutrophils", J. Leukocyte Biol, 2014, vol. 96, p. 1-8.
diZerega, G.S. et al., (1992) "Prevention of Postoperative Adhesions in The Peritoneum" Eds. Springer-Verlag, New York, pp. 307-369.
Dunford, P.J., et al., "The Histamine H4 Receptor Drives Inflammation in Preclinical Models of Arthritis", American College of Rheumatology, 2013.
Dunford, P.J., et al., Hansel TT, Barnes PJ (eds): "Histamine H4 receptor antagonists", New Drugs and Targets for Asthma and COPD., Prog Respir Res. Basel, Karger 2010, vol. 39, pp. 187-191.
Edwards, J. P.,"Ten(+) Years of Histamine H4 Antagonists at Janssen", The Scott E. Denmark Symposium, University of Illinios, Urbana-Champaign, IL. Aug. 3, 2013.
Edwards, J. P., "Ten(+) Years of Histamine H4 Antagonists at Janssen", GTC Novel Immunotherapeutics Summit, Jan. 31, 2013.
Edwards, J. P. "What's Out *There*?" University of California, San Diego, Jan. 13, 2014.
Engelhardt, H. et al., "A New Generation of Anti-Histamines: Histamine H4 Receptor Antagonists on Their Way to the Clinic", Curr. Opin. Drug Disc. Dev., 2009, 12(5), 628-643.
English, et al., Journal of the American Chemical Society, 1946, 68, 1039-1049.
Fei, F., et al., "New substituted benzimidazole derivatives: a patent review (2010-2012)", Expert Opin. Ther. Patents (2013) 23(9).
Igel, P., et al., "Histamine H4 receptor agonists", Bioorganic & Medicinal Chemistry Letters, 20 (2010) 7191-7199.
Istyastono, E. P., et al, "Molecular Determinants of Selective Agonist and Antagonist Binding to the Histamine H4 Receptor", Current Topics in Medicinal Chemistry, 2011, 11, 661-679.
Kamo, A., et al., "Histamine H4 Receptor Antagonists Ineffective against Itch and Skin Inflammation in Atopic Dermatitis Mouse Model", Journal of Investigative Dermatology (2014) 134, 546-548.
Kiss, R., et al., "Histamine H4 receptor ligands and their potential therapeutic applications: an update", Expert Opin. Ther. Patents (2012) 22(3).
Kumar et al., "Design, Synthesis and Biological Evaluation of 1,3-diaminopropanes: A new Class of Polyamine Analogs as Leishmanicidal Agents", Bioorg Med Chem Lett, 1997, 7(6), 675-680.
Lee, A. et al., "Development of Benzimidazole Ligands for the H4 Receptor", 229th ASC National Meeting, San Diego, CA, United States, Mar. 13-17, 2005, MEDI-052.
Lim, H.D., et al. "Molecular determinants of ligand binding to H4R species variants" Mol. Pharmacol. 2010, 77 (5), 734-743.
Lochner, S. and Broggini, D. "Impurity Management Progressing from Early to Late Phase Development", $30^{th}$ SCI Process Development Symposium, Cambridge, England, Dec. 7, 2012.
Charles M. Marson, "Targeting the Histamine H4 Receptor", Chem. Rev. 2011, 111, 7121-7156.
Saskia Nijmeijer,, et al, "Molecular pharmacology of histamine H4 receptors", Frontiers in Bioscience, 17, 2089-2106, Jun. 1, 2012.
Onuma, S. "Usefulness of the histamine $H_4$ receptor antagonist on exacerbation of pruritus induced by long-term topical steroids treatment", Japanese Society of Toxicology Jul. 2-4, 2014.
Popov, A. et al., "Spontaneous Gelation of a Novel Histamine H4 Receptor Antagonist in Aqueous Solution", Pharm Res (2011) 28:2556-2566.
Rodgers, K.E., et al., (1990) "Nonsteroidal Anti-Inflammatory Drugs (NSAIDs) in the treatment of Postsurgical Adhesion" Treatment of Post-Surgical Adhesions, pp. 119-129.
Savall, B.M., et al. "Agonist/antagonist modulation in a series of 2-aryl benzimidazole H4 receptor ligands" Bioorg Med Chem Lett, 2010, 20(11), 3367-3371.

(56) References Cited

OTHER PUBLICATIONS

Savall, B.M. et al., "6-Alkyl-2-aminopyrimidines as Potent Histamine H4 Receptor Antagonists", Gordon Research Conference Medicinal Chemistry, Aug. 5-10, 2012.
Savall, B.M., et al., Selective phenol alkylation for an improved synthesis of 2-arylbenzimidazole H4 receptor ligands, Tetrahedron Letters 50 (2009) 2490-2492.
Savall, B. M., et al., "Discovery and SAR of 6-Alkyl-2,4-diaminopyrimidines as Histamine H4 Receptor Antagonists", J. Med. Chem. 2014, 57(6), 2429-2439.
Savall, B. M. et al., "Tricyclic aminopyrimidine histamine H4 receptor antagonists", Bioorganic & Medicinal Chemistry Letters 21 (2011) 6577-6581.
Schneider E.H., et al. "Structural requirements for inverse agonism and neutral antagonism of indole-, benzimidazole-, and thienopyrrole-derived histamine H4 receptor ligands" J. Pharmacol Exp Ther 2010, 334 (2) 513-521.
Short et al., "Sympathetic Nervous System Blocking Agents. Derivatives of Guanidine and Related Compounds." J. Med. Chem., 1963, 6, 275-283.
Thurmond et al "A Potent and Selective Histamine $H_4$ Receptor Antagonist with Anti-Inflammatory Properties" J Pharmacol Exp Ther 2004 vol. 309(1) pp. 404-413.
Thurmond, R. L.; "The Role of the Histamine $H_4$ Receptor in Allergy and Inflammation", European Histamine Research Society Meeting Sochi, Russia May 13, 2011.
Thurmond, R. L.; "Clinical Development of Histamine $H_4$ Receptor Antagonists", Lecture at University of Hanover, Germany May 12, 2014.
Thurmond, R. L.; "The Role of the Histamine $H_4$ Receptor in Allergy and Inflammation", Lecture at University of Hanover, Germany May 17, 2011.
Thurmond, R. L.; "The Histamine $H_4$ Receptor and Immune Function", Japanese Society of Immunotoxicity, Chiba, Japan Sep. 8, 2011.
Thurmond, R. L.; "Frontiers in Histamine Research", American Academy of Allergy, Asthma and Immunology, San Francisco, CA, Mar. 18-22, 2011.
Thurmond, R. L.; "The Role of the Histamine H4 Receptor in Allergy and Inflammation", Allergy Drug Discovery and Development Conference, San Diego, CA Jan. 30, 2012.
Thurmond, R. L.; "Novel Antihistamines that Target the Histamine $H_4$ Receptor", Experimental Biology Meeting, San Diego, CA, Apr. 22, 2012.
Thurmond, R.L., "The Development of Histamine $H_4$ Receptor Antagonists", Japanese Society of Toxicology—Chiba Japan Jun. 18, 2013.
Thurmond, R. L. et al., "The Histamine $H_4$ Receptor Mediates Inflammation and Pruritus in Th2-dependent Dermal Inflammation", International Congress of Immunology, Kobe, Japan Aug. 22-27, 2010.
Thurmond, R. L.; "Histamine H4 Receptor Antagonists New Antihistamines for Itch", 21st Annual Meeting of the International Symposium of Itch,Osaka, Japan Oct. 29, 2011.
Thurmond, R. L.; "The Role of the Histamine H4 Receptor in Allergy and Inflammation", Lecture at University of Vermont, Burlington, VT Nov. 5, 2010.
Thurmond, R. L.; "The Histamine H4 Receptor and Immune Function", Lecture at Tohoku University Sendai, Japan Sep. 7, 2011.
Thurmond, R. L.; "The Role of the Histamine H4 Receptor in Allergy and Inflammation", Lecture at Queen's University Belfast, UK May 1, 2012.
Thurmond, R. L.; "Histamine H4 Receptor Antagonists as Future Anti-Inflammatory Drugs", 27th Noordwijkerhout-Camerino-Cyprus Symposium, Noordwijkerhout, Netherlands, May 5, 2009.
Thurmond, R. L., et al, "Clinical and Preclinical Characterization of the Histamine H4 Receptor Antagonist JNJ-39758979", J Pharmacol Exp Ther 349:176-184, May 2014.
Mitsutoshi Tominaga, "Histamine $H_4$ receptor antagonists ineffective against itch and skin inflammation in atopic dermatitis mouse model", $7^{th}$ World Congress on Itch (WCI) Sep. 21-23, 2013, Boston, USA, Oral Presentation, Abstract provided.
Mitsutoshi Tominaga. International Investigative Dermatology, "Histamine $H_4$ receptor antagonists exhibit insufficient anti-pruritic and anti-inflammatory effects on mite extract ointment-induced mouse model of atopic dermatitis", May 8-11, 2013, Edinburgh, Scotland, Oral Presentation, Abstract provided.
Mitsutoshi Tominaga , "Histamine $H_4$ receptor antagonists exhibit insufficient anti-pruritic and anti-inflammatory effects on mite extract ointment-induced mouse model of atopic dermatitis", International Investigative Dermatology, May 8-11, 2013, Edinburgh, Scotland.
Two application statements on a non-proprietary name adopted by the USAN Council dated May 28, 2014.
Venable, J.D., et al. "Development and chemistry of histamine H4 receptor ligands as potential modulators of inflammatory and allergic diseases" Anti-Inflamm Anti-Allergy Agents in Med Chem. 2006, 5 (4), 307-322.
Venable, J. "Discovery, SAR, and functional consequences of various 2-heteroarylbenzimidazoles at the human histamine H4 receptor of 2-heteroarylbenzimidazoles", 67th Southwest Regional Meeting of the American Chemical Society, Austin, TX, United States, Nov. 9-12, 2011, SWRM-183.
Venable, J. "Synthesis and SAR of 2-Pyridinylbenzimidazoles as Human Histamine $H_4$ Antagonists", CHI Drug Discovery Chemistry, Apr. 27-28, 2010 • San Diego, CA.
Venable, J, "Novel Modulators of the Human Histamine $H_4$ Receptor", California Institute of Technology, Pasadena, California Apr. 6, 2011.
Venable, J, "Discovery and Development of Human Histamine $H_4$ Antagonists", Medicinal Chemistry Symposium, University of California, San Diego, Jul. 12, 2013.
Venable J., "Synthesis and SAR of 2-Pyridinylbenzimidazoles as Human Histamine $H_4$ Antagonists", 239th ACS National Meeting, San Francisco, CA, United States, Mar. 21-25, 2010, MEDI-14.
Walter, M., et al., "Histamine receptor subtypes: a century of rational drug design", Frontiers in Bioscience S4, 461-488, Jan. 1, 2012.
Katsunori Yamaura, Joint Symposium of The Japanese Society of Toxicology and The Japanese Society of Immunotoxicology, "Long-term topical steroids treatment and skin toxicity characterized by pruritus" Jul. 2014, Oral Presentation.
Cheong, et al., "Peritoneal Healing and Adhesion Formation/Reformation," Human Reproduction Update, vol. 7, No. 6, pp. 556-566 (2001).
Anisman et al., "Interleukin-1b Production in Dysthymia before and after Pharmacotherapy", Society of Biological Psychiatry, 1999;46:1649-1655.
Stahl et al., Handbook of Pharmaceutical Salts, Properties, Selection and Use, Eds., Wiley-VCH and VHCA, Zurich 2002.
Yildiz, M.K., et al., *Int J Clin Exp Med*. 2014; 7(2): 405-410, "Effect of orally administered simvastatin on prevention of postoperative adhesion in rats".
Practice Committee of the American Society for Reproductive Medicine in collaboration with the Society of Reproductive Surgeons, Fertility and Sterility, 2013, 99,( 6), 1550-1555, "Pathogenesis, consequences, and control of peritoneal adhesions in gynecologic surgery: a committee opinion".
Ural, A.U. et al., *Annals of Surgery*, 2008, 247, (1), 203-205, "Bisphosphonates May Increase Peritoneal Fibrinolytic Activity by Inhibiting the Mevalonate Pathway".
Lim, R., et al., *J Gastrointest Surg* (2008) 12:1754-1761, "An FDA Approved Neurokinin-1 Receptor Antagonist is Effective in Reducing Intraabdominal Adhesions when Administered Intraperitoneally, But Not Orally".
Aarons, Cary B., et al., Annals of Surgery, 2007, 245, (2), 176-184, "Statins HHMG-CoA Reductase Inhibitors) Decrease Posoperative Adhesions by Increasing Peritoneal Fibrinolytic Activity."
Siegel et al, "Rapid Parallel Synthesis Applied to the Optimization of a Series of Potent Nonpeptide Neuropeptide Y-1 Receptor Antagonists", *Tetrahedron* (1995) 55:11619-11639.
Song et al, "Synthesis of Cyclic Prodrugs of Aggrastat and Its Analogue with a Modified Phenylpropionic Acid Linker", *Organic Letters* (2002) 4(4):549-552.

(56) References Cited

OTHER PUBLICATIONS

Alberola et al., "Based-Induced Ring Cleavage of 4-Functionalized 3-Unsubstituted Isoxazoles. Synthesis of 2-Aminopyrimidines and Pyrimidine-2(3H)-Thiones", National Taiwan University Library, vol. 25, 1987, pp. 393-397.

Yu, Fuqu, et al. "Pharmacological characterization of oxime agonists of the histamine H4 receptor." J. Receptor Ligand Channel Res 3 (2010): 37-49.

Roβbach, Kristine, et al. "Histamine H4 receptor antagonism reduces hapten-induced scratching behaviour but not inflammation." Experimental dermatology 18.1 (2009): 57-63.

Leonardi, A., et al. "Histamine H4 receptors in normal conjunctiva and in vernal keratoconjunctivitis." Allergy 66.10 (2011): 1360-1366.

Massari, N. A., et al. "Role of H4 receptor in histamine-mediated responses in human melanoma." Melanoma research 21.5 (2011): 395.

Medina, V. A., et al. "Role of histamine H4 receptor in breast cancer cell proliferation." Frontiers in bioscience (Elite edition) 3 (2010): 1042-1060.

Fang, Zhengyu, et al. "Attenuated expression of HRH4 in colorectal carcinomas: a potential influence on tumor growth and progression." BMC cancer 11.1 (2011): 195.

Strakhova, Marina I., et al. "Localization of histamine H$_4$ receptors in the central nervous system of human and rat." Brain research 1250 (2009): 41-48.

Coruzzi, Gabriella, et al. "Antiinflammatory and antinociceptive effects of the selective histamine H4receptor antagonists JNJ7777120 and VUF6002 in a rat model of carrageenan-induced acute inflammation." European journal of pharmacology 563.1 (2007): 240-244.

Cowart, Marlon D., et al. "Rotationally constrained 2, 4-diamino-5, 6-disubstituted pyrimidines: a new class of histamine H4 receptor antagonists with improved druglikeness and in vivo efficacy in pain and inflammation models." Journal of medicinal chemistry 51.20 (2008): 6547-6557.

Hsieh, Gin C., et al. "H$_4$ receptor antagonism exhibits anti-nociceptive effects in inflammatory and neuropathic pain models in rats." Pharmacology Biochemistry and Behavior 95.1 (2010): 41-50.

Liu, Huaqing, et al. "cis-4-(Piperazin-1-yl)-5, 6, 7a, 8, 9, 10, 11, 11a-octahydrobenzofuro [2, 3-h] quinazolin-2-amine (A-987306), a new histamine H4R antagonist that blocks pain responses against carrageenan-induced hyperalgesia." Journal of medicinal chemistry 51.22 (2008): 7094-7098.

Krogsgaard-Larsen, Povl. A textbook of drug design and development. Harwood Academic Pub, 1991.

Alfon, et al., Inflamm. Res. 2010; 59 (Suppl 2): S199-200.

Ye, F. et al., 2014 ARVO Meeting Abstract, Program #/3291, Board #C0223, Histamine Receptor H4 as a New Therapeutic Target for Choroidal Neovascularization in Age-related macular degeneration).

Gill, D. S., C. S. Thompson, and P. Dandona. "Increased histamine in plasma and tissues in diabetic rats." Diabetes research (Edinburgh, Scotland) 7.1 (1988): 31-34.

Rosa, A. C., et al. "Overexpression of histamine H4 receptors in the kidney of diabetic rat." Inflammation Research 62.4 (2013): 357-365.

Bundgaard, Hans. "(C) Means to enhance penetration:(1) Prodrugs as a means to improve the delivery of peptide drugs." Advanced Drug Delivery Reviews 8.1 (1992): 1-38.

Bell, J. K., D. S. McQueen, and J. L. Rees. "Involvement of histamine H4 and H1 receptors in scratching induced by histamine receptor agonists in BalbC mice." British Journal of Pharmacology 142.2 (2004): 374-380.

Kaneko et al., "Histamine J4 receptor as a new therapeutic target for choroidal neovascularization in age-related macular degeneration", British Journal of Pharmacology 171 (2014) 3754-3763.

Matsuda, N., et al., "Up-Regulation of Histamine H4 Receptors Contributes to Splenic Apoptosis in Septic Mice: Counteraction of the Antiapoptotic Action of Nuclear Factor-kB", J. Pharmacol. Exp. Ther., 2010, 332, 730-737.

Kim, Yong-Ku et al., "Cytokine imbalance in the pathophysiology of major depressive disorder", Progress in Neuro-Psychopharmacology & Biological Psychiatry 31 (2007) 1044-1053.

Jack D. Dunitz and Joel Bernstein, "Disappearing Polymorphs", Acc. Chem. Res., 1995, vol. 28, No. 4, pp. 193-200.

John K. Haleblian and Walter Mccrone, "Pharmaceutical Applications of Polymorphism", Journal of Pharmaceutical Sciences, 1969, vol. 58, No. 8, pp. 911-929.

John K. Haleblian, "Characterization of Habits and Crystalline Modification of Solids and Their Pharmaceutical Applications", Journal of Pharmaceutical Sciences, 1975, vol. 64, No. 8, pp. 1269-1288.

Slater, A., et al., "Increase in epithelial mast cell numbers in the nasal mucosa of patients with perennial allergic rhinitis", Journal of Laryngology and Otology, Oct. 1996, vol. 110, pp. 929-933.

\* cited by examiner

BENZOIMIDAZOL-2-YL PYRIMIDINES AND PYRAZINES AS MODULATORS OF THE HISTAMINE H4 RECEPTOR

This application is a continuation of U.S. patent application Ser. No. 14/051,962, filed Oct. 11, 2013, which is a continuation of U.S. patent application Ser. No. 13/676,595, filed Nov. 14, 2012, now U.S. Pat. No. 8,598,189, issued on Dec. 3, 2013, which is a continuation of U.S. patent application Ser. No. 12/816,995, filed Jun. 16, 2010, now U.S. Pat. No. 8,343,989, issued on Jan. 1, 2013, which in turn is a continuation of U.S. patent application Ser. No. 12/321,208, filed Jan. 15, 2009, now abandoned, which in turn is a continuation of U.S. patent application Ser. No. 11/731,074, filed Mar. 30, 2007, now U.S. Pat. No. 7,507,737, issued on Mar. 24, 2009, which claims the benefit of U.S. provisional patent application Ser. No. 60/788,190, filed on Mar. 31, 2006, all of which are incorporated herein by reference.

FIELD OF THE INVENTION

The present invention relates to certain benzoimidazol-2-yl pyrimidines and pyrazines, pharmaceutical compositions containing them, and methods of using them for the treatment of disease states, disorders, and conditions mediated by histamine $H_4$ receptor activity.

BACKGROUND OF THE INVENTION

The histamine $H_4$ receptor ($H_4R$) is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), $CD8^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$, receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$, receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in $CD8^+$ T cells has also been reported. Gantner, et al., (2002) showed that both $H_4$ and $H_2$ receptors control histamine-induced IL-16 release from human CD8+ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in $CD4^+$ cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that H₄ receptor antagonists have the capacity to be anti-inflammatory in vivo.

Another physiological role of histamine is as a mediator of itch and H₁ receptor antagonists are not completely effective in the clinic. Recently, the H₄ receptor has also been implicated in histamine-induced scratching in mice (Bell, J. K., et al., Br. J. Pharmacol. 2004, 142(2), 374-380). The effects of histamine could be blocked by H₄ antagonists. These results support the hypothesis that the H₄ receptor is involved in histamine-induced itch and that H₄ receptor antagonists will therefore have positive effects in treating pruritis.

Modulation of H₄ receptors controls the release of inflammatory mediators and inhibits leukocyte recruitment, thus providing the ability to prevent and/or treat H₄-mediated diseases and conditions, including the deleterious effects of allergic responses such as inflammation. Compounds according to the present invention have H₄ receptor modulating properties. Compounds according to the present invention have leukocyte recruitment inhibiting properties. Compounds according to the present invention have anti-inflammatory properties.

Examples of textbooks on the subject of inflammation include: 1) Gallin, J. I.; Snyderman, R., *Inflammation: Basic Principles and Clinical Correlates,* 3rd ed.; Lippincott Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al. *Textbook Of Medicine,* 18th ed.; W.B. Saunders Co., 1988; and 4) Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Thus, small-molecule histamine H₄ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritis, and immunodeficiency disorders. Diseases, disorders and medical conditions that are mediated by histamine H₄ receptor activity include those referred to herein. 2-Arylbenzimidazoles have been described as histamine H₄ receptor modulators, see, for example, U.S. Pat. Appl. Publ. 2005/0070550A1. However, there still remains a need for potent histamine H₄ receptor modulators with desirable pharmaceutical properties.

SUMMARY OF THE INVENTION

Certain benzoimidazol-2-yl pyrimidines and pyrazines have now been found to have histamine H₄ receptor-modulating activity.

In one general aspect, the invention relates to compounds of the following Formula (I):

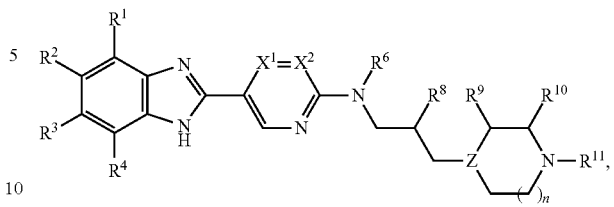

(I)

wherein
each of $R^{1\text{-}4}$ is independently H, $C_{1\text{-}4}$alkyl, $C_{2\text{-}4}$alkenyl, $C_{2\text{-}4}$alkynyl, phenyl, —$CF_3$, —$OCF_3$, —CN, halo, —$NO_2$, —$OC_{1\text{-}4}$alkyl, —$SC_{1\text{-}4}$alkyl, —$S(O)C_{1\text{-}4}$alkyl, —$SO_2C_{1\text{-}4}$alkyl, —$C(O)C_{1\text{-}4}$alkyl, —C(O)phenyl, —$C(O)NR^aR^b$, —$CO_2C_{1\text{-}4}$alkyl, —$CO_2H$, —$C(O)NR^aR^b$, or —$NR^aR^b$; wherein $R^a$ and $R^b$ are each independently H, $C_{1\text{-}4}$alkyl, or $C_{3\text{-}7}$cycloalkyl;
one of $X^1$ and $X^2$ is N and the other is C—$R^c$;
where $R^c$ is H, methyl, hydroxymethyl, dimethylaminomethyl, ethyl, propyl, isopropyl, —$CF_3$, cyclopropyl, or cyclobutyl;
n is 1 or 2;
Z is N, CH, or C($C_{1\text{-}4}$alkyl);
$R^6$ is H, $C_{1\text{-}6}$alkyl, or monocyclic cycloalkyl;
$R^8$ is H or $C_{1\text{-}4}$alkyl;
$R^9$ and $R^{10}$ are each independently H or $C_{1\text{-}4}$alkyl; and
$R^{11}$ is H or $C_{1\text{-}4}$alkyl.

This invention also relates to any of the following: pharmaceutically acceptable salts of compounds of Formula (I), pharmaceutically acceptable prodrugs of compounds of Formula (I), and pharmaceutically active metabolites of compounds of Formula (I).

In other embodiments, the compound of Formula (I) is a compound selected from those species described or exemplified in the detailed description below.

In a further general aspect, the invention relates to pharmaceutical compositions each comprising: (a) an effective amount of at least one agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by histamine H₄ receptor activity, comprising administering to the subject in need of such treatment an effective amount of at least one compound of Formula (I), or a pharmaceutically acceptable salt, pharmaceutically acceptable prodrug, or pharmaceutically active metabolite of such compound. In certain preferred embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

In another general aspect, the invention is directed to a method for modulating histamine H₄ receptor activity, comprising exposing histamine H₄ receptor to an effective amount of at least one of a compound of Formula (I) and a salt thereof.

Additional embodiments, features, and advantages of the invention will be apparent from the following detailed description and through practice of the invention.

DETAILED DESCRIPTION OF INVENTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two sp$^2$ hybridized carbon atoms.) Illustrative alkenyl groups include prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

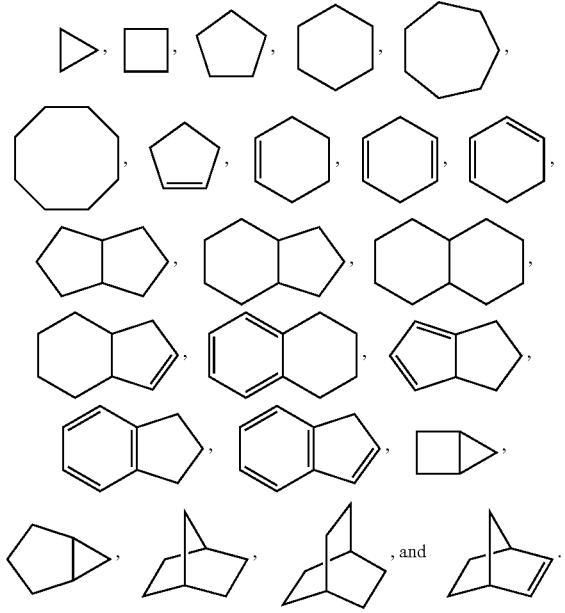

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

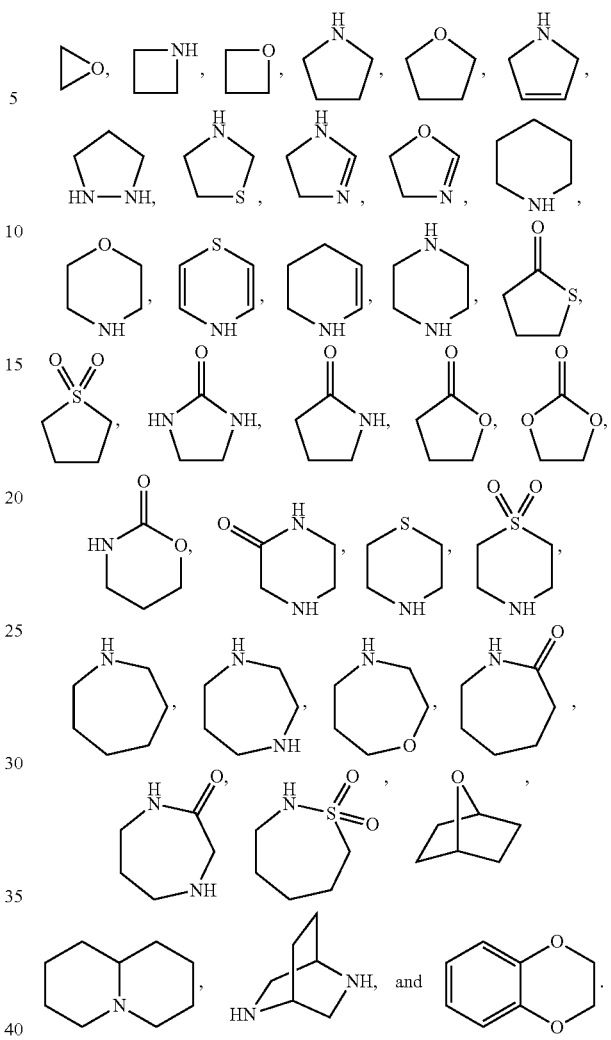

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

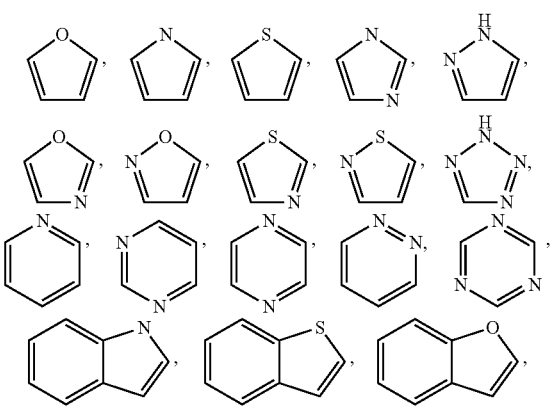

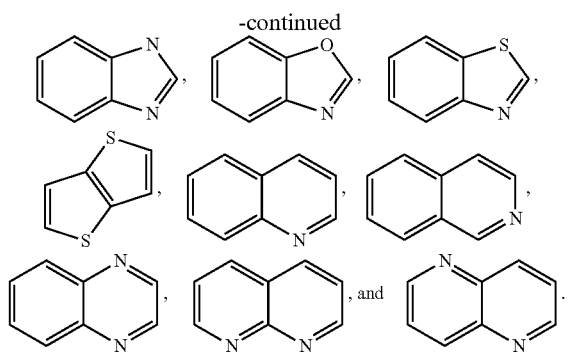

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. In another example, a zwitterionic compound is encompassed herein by referring to a compound that is known to form a zwitterions, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. (See, for example its on line version at http://www.ebi.ac.uk/chebi/init.do). As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$, and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$, and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-11}$, $X^1$, $X^2$, and n, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-11}$, $X^1$, $X^2$, and n, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$, refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formula (I), each of $R^{1-4}$ is independently H, methyl, tert-butyl, methoxy, —$CF_3$, —CN, fluoro, chloro, methoxycarbonyl, or benzoyl.

In some embodiments, $X^2$ is N. In other embodiments, $X^1$ is N.

In some embodiments, $R^c$ is H, methyl, ethyl, $CF_3$, cyclopropyl, or cyclobutyl. In further embodiments, $R^c$ is H or methyl.

In some embodiments, n is 1.

In some embodiments, Z is N or CH. In further embodiments, Z is CH.

In some embodiments, $R^6$ is H, methyl, ethyl, propyl, isopropyl, cyclopropyl, or cyclobutyl. In further embodiments, $R^6$ is H or methyl.

In some embodiments, $R^8$ is H.

In some embodiments, $R^9$ and $R^{10}$ are each independently H or methyl. In further embodiments, $R^9$ and $R^{10}$ are both H.

In some embodiments, $R^{11}$ is H or methyl. In further embodiments, $R^{11}$ is methyl.

The invention includes also pharmaceutically acceptable salts of the compounds represented by Formula (I), preferably of those described above and of the specific compounds exemplified herein.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to treatment methods employing pharmaceutically acceptable prodrugs of the compounds of Formula (I). The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl)amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Adv. Drug Delivery Rev. 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in J. Med. Chem. 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., J. Med. Chem. 1997, 40, 2011-2016; Shan, et al., J. Pharm. Sci. 1997, 86 (7), 765-767; Bagshawe, Drug Dev. Res. 1995, 34, 220-230; Bodor, Adv. Drug Res. 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as histamine $H_4$ receptor modulators in the methods of the invention. The agents may be used in the inventive methods for the treatment or prevention of medical conditions, diseases, or disorders mediated through modulation of the histamine $H_4$ receptor, such as those described herein. Agents according to the invention may therefore be used as an anti-inflammatory agents. Symptoms or disease states are intended to be included within the scope of "medical conditions, disorders, or diseases."

Accordingly, the invention relates to methods of using the pharmaceutical agents described herein to treat subjects diagnosed with or suffering from a disease, disorder, or condition mediated through histamine $H_4$ receptor activity, such as inflammation.

In a preferred embodiment, an agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with a histamine $H_4$ receptor-modulating agent according to the invention include inflammation due to or associated with any one of a plurality of conditions such as allergy, asthma, dry eye, chronic obstructed pulmonary disease (COPD), atherosclerosis, rheumatoid arthritis, multiple sclerosis, inflammatory bowel diseases (including colitis, Crohn's disease, and ulcerative colitis), psoriasis, pruritis, itchy skin, atopic dermatitis, urticaria (hives), ocular inflammation, conjunctivitis, nasal polyps, allergic rhinitis, nasal itch, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritis with a histamine $H_4$ receptor-modulating agent according to the invention includes that which is a symptom of allergic cutaneous diseases (such as atopic dermatitis and hives) and other metabolic disorders (such as chronic renal failure, hepatic cholestasis, and diabetes mellitus).

In another preferred embodiment, an agent of the present invention is administered to treat allergy, asthma, autoimmune diseases, or pruritis.

The term "treat" or "treating" as used herein is intended to refer to administration of an agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least one pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An example of a dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an illustrative embodiment, additional active compounds are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

The agents of the invention are used, alone or in combination with one or more other active ingredients, to formulate pharmaceutical compositions of the invention. A pharmaceutical composition of the invention comprises an effective amount of at least one pharmaceutical agent in accordance with the invention. A pharmaceutically acceptable excipient is part of some embodiments of pharmaceutical compositions according to this invention.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the agent and any other active ingredients mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Examples of liquid oral excipients include ethanol, glycerol, water, and the like. Starch, polyvinyl-pyrrolidone (PVP), sodium starch glycolate, microcrystalline cellulose, and alginic acid are examples of disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Examples of agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

In the Schemes depicted below, one skilled in the art will recognize that $R^{11}$ may be replaced with a suitable nitrogen protecting group, such as a tert-butoxycarbonyl group (Boc), and that protecting group replaced at a later stage in the synthesis.

SCHEME A

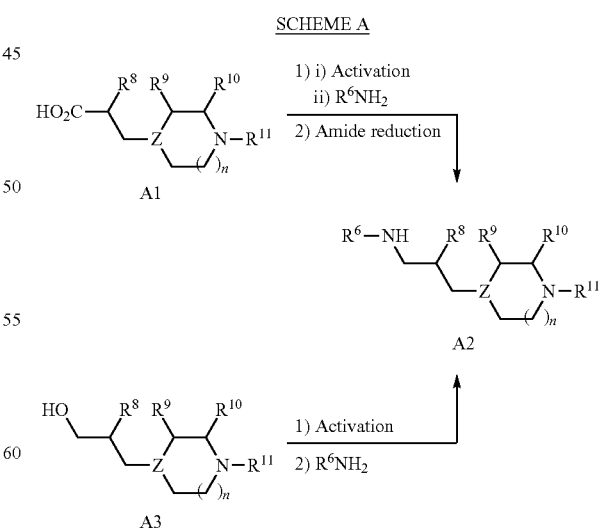

Referring to Scheme A, amines A2 are commercially available or are prepared from acids A1 or alcohols A3. Coupling of acids A1 with amines $R^6NH_2$, in the presence of activating agents such as dicyclohexyl-carbodiimide, EDC/HOBt, or carbonyl diimidazole, in a solvent such as DMF or THF, provides the corresponding amides (not shown). Alternatively, acids A1 are activated to their corresponding acid chlorides and reacted with amines $R^6NH_2$ in the presence of a suitable base such as triethylamine or diisopropylethylamine, in a solvent such as DCM or THF. The resulting amides are reduced to amines A2 by a suitable reducing agent such as $LiAlH_4$, in a solvent such as THF. Alcohols A3 are activated using general methods to form, for example, alkyl halides or alkyl tosylates. Displacement with $R^6NH_2$ in the presence of a suitable base such as NaH, NaOH, triethylamine, or diisopropylethylamine, in a solvent such as DCM or THF, provides amines A2. Alternatively, amines A2 are prepared from alcohols A3 by reaction with phthalimide or a suitable amino surrogate under Mitsunobu conditions. Where phthalimide is used, the free amine is revealed through treatment with hydrazine.

corresponding alcohols (not shown). Where an alcohol is produced, oxidation using a suitable oxidizing agent such as $MnO_2$, Dess-Martin periodinane, or Swern conditions, provides aldehydes B3. Condensation of aldehydes B3 with suitably substituted diamines B4, in the presence of a dehydrating agent such as $NaH_2S_2O_5$, in a solvent such as DMF, MeOH, or EtOH, or a mixture thereof, at temperatures between about room temperature and the reflux temperature of the solvent, produces compounds of Formula (I).

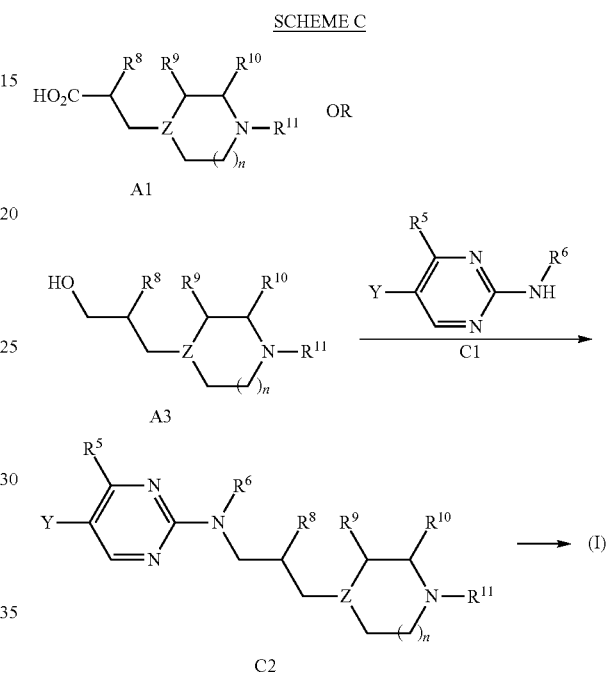

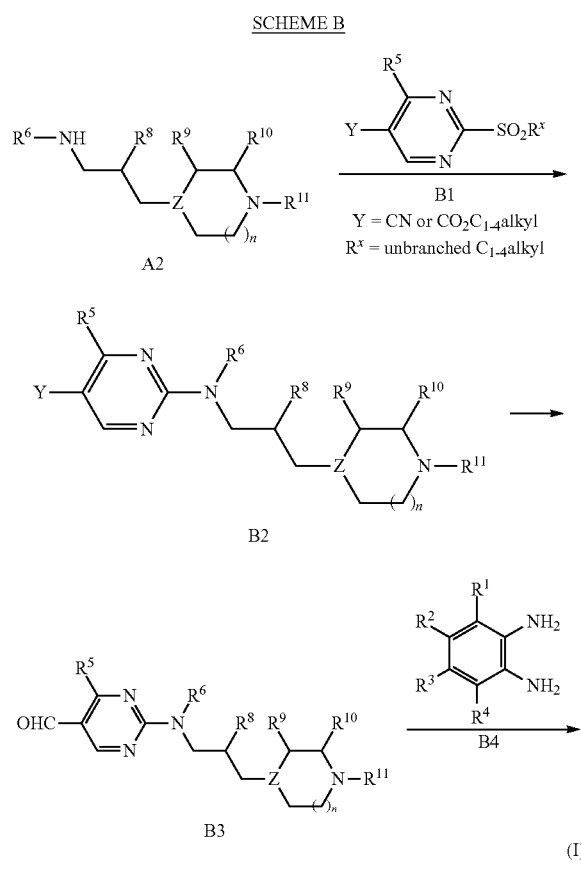

Referring to Scheme B, amines A2 are reacted with pyrimidines B1, which are commercially available or are prepared by oxidation of commercially available alkylsulfanyl pyrimidines, or by other general methods, in a solvent such as pyridine, DMF, MeOH, or EtOH, or a mixture thereof, at temperatures between about room temperature and the reflux temperature of the solvent, or in a sealed tube at temperatures up to about 120° C. 2-Aminopyrimidines B2 are converted to aldehydes B3 by reduction of the Y substituent with a suitable reducing agent such as diisobutylaluminum hydride. Where Y is an ester group, reduction produces aldehydes B3 or the Referring to Scheme C, acids A1 or alcohols A3 may be coupled with 2-aminopyrimidines C1 using the methods described in Scheme A to form amides and amines C2. Compounds C2 are processed as described in Scheme B to provide compounds of Formula (I).

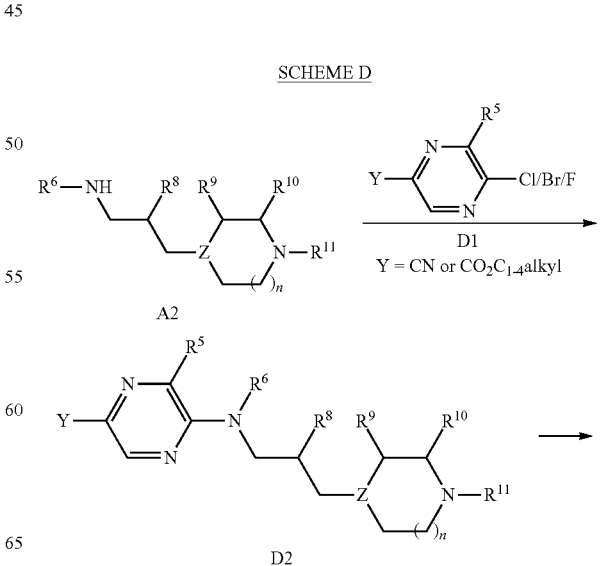

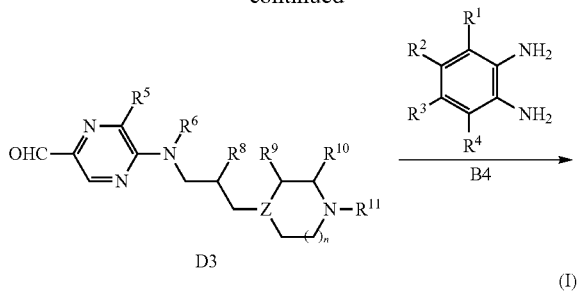

Referring to Scheme D, amines A2 are reacted with pyrazines D1, which are commercially available or are prepared by general methods, in a solvent such as pyridine, MeOH, or EtOH, or a mixture thereof, at temperatures between about room temperature and the reflux temperature of the solvent, or in a sealed tube at temperatures up to about 120° C. 2-Aminopyrazines D2 are processed into compounds of Formula (I) as shown in Scheme D using methods analogous to those described in Scheme B.

Additional synthetic methods are described in U.S. Pat. Appl. Publ. 2005/0070550A1, which is hereby incorporated by reference.

Compounds prepared according to the schemes described above may be obtained as single enantiomers, diastereomers, or regioisomers, or as racemic mixtures or mixtures of enantiomers, diastereomers, or regioisomers. Where regioisomeric or diastereomeric mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, diastereomeric salt formation, or derivatization into diastereomeric adducts followed by separation.

The following examples are provided to further illustrate aspects of the invention and various preferred embodiments.

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal-phase flash column chromatography (FCC) was performed on silica gel ($SiO_2$) eluting with 2 M $NH_3$ in MeOH/DCM, unless otherwise noted. Reaction mixtures were loaded onto the $SiO_2$ column without workup.

Reversed-phase HPLC was performed on a Hewlett Packard HPLC Series 1100, with a Phenomenex Luna C18 (5 μm, 4.6×150 mm) column. Detection was done at λ=230, 254 and 280 nm. The gradient was 10 to 99% acetonitrile/water (0.05% trifluoroacetic acid) over 5.0 min with a flow rate of 1 mL/min. Alternatively, HPLC was performed on a Dionex APS2000 LC/MS with a Phenomenex Gemini C18 (5 μm, 30×100 mm) column, and a gradient of 5 to 100% acetonitrile/water (20 mM $NH_4OH$) over 16.3 min, and a flow rate of 30 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

Chemical names were generated using ChemDraw Version 6.0.2 (CambridgeSoft, Cambridge, Mass.).

Example 1

[5-(5-Fluoro-4-methyl-1H-benzoimidazol-2-yl)-4-methyl-pyrimidin-2-yl]-[3-(1-methyl-piperidin-4-yl)-propyl]-amine

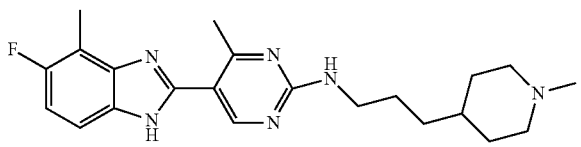

Step A;
4-Methyl-2-ethylsulfanyl-pyrimidine-5-carboxylic acid ethyl ester

A mixture of ethyl acetoacetate (6.37 mL, 50.0 mol), dimethylformamide dimethylacetal (8.94 g, 75.0 mmol), and catalytic p-toluenesulfonic acid was heated at 100° C. for 2 h. After cooling to rt, the mixture was diluted with N,N-dimethylformamide (DMF; 50 mL) and 2-ethylisothiourea hydrobromide (9.10 g, 50.0 mmol) was added. After heating the at 100° C. for 18 h, the mixture was cooled to rt and concentrated to give a crude residue, which was purified by FCC (EtOAc/hexanes) to give 7.1 g (61%) of a solid. $^1H$ NMR ($CDCl_3$): 8.97-8.91 (m, 1H), 4.43-4.35 (m, 2H), 3.24-3.15 (m, 2H), 2.81-2.72 (m, 3H), 1.47-1.35 (m, 6H).

Step B;
2-Ethanesulfonyl-4-methyl-pyrimidine-5-carboxylic acid ethyl ester

To a 0° C. solution of 4-methyl-2-ethylsulfanyl-pyrimidine-5-carboxylic acid ethyl ester (3 g, 13.3 mmol) in dichloromethane (DCM; 50 mL) was added urea hydrogen peroxide (5.20 g, 55.7 mmol) followed by trifluoroacetic anhydride (7.39 mL, 53.1 mmol) dropwise. The solution was warmed to rt for 2 h before quenching with satd. aq. $Na_2S_2O_3$ (20 mL) and extracting with DCM (100 mL). The organic layer was dried (Na$_2$SO$_4$) and concentrated to give 1.50 g of an orange solid which was used immediately in the next step without purification. $^1$H NMR (CDCl$_3$): 9.28 (s, 1H), 4.47 (q, J=7.2 Hz, 2H), 3.60 (q, J=7.5 Hz, 2H), 2.96 (s, 3H), 1.47-1.42 (m, 6H).

Step C; 4-Methyl-2-[3-(1-methyl-piperidin-4-yl)-propylamino]-pyrimidine-5-carboxylic acid ethyl ester A mixture of 2-ethanesulfonyl-4-methyl-pyrimidine-5-carboxylic acid ethyl ester (0.30 g, 1.18 mmol) and 3-(1-methyl-piperidin-4-yl)-propylamine (0.18 mg, 1.10 mmol) in EtOH (3 mL) was heated in a sealed tube at 100° C. for 6 h. The mixture was concentrated and purified by FCC to give 200 mg (53%). $^1$H NMR (CDCl$_3$): 8.88-8.72 (m, 1H), 5.60-5.44 (m, 1H), 4.31 (q, J=7.2 Hz, 2H), 3.52-3.39 (m, 2H), 2.91-2.77 (m, 2H), 2.64 (s, 3H), 2.26 (s, 3H), 1.94-1.85 (m, 2H), 1.72-1.57 (m, 4H), 1.41-1.20 (m, 8H).

Step D; {4-Methyl-2-[3-(1-methyl-piperidin-4-yl)-propylamino]-pyrimidin-5-yl}-methanol To a 0° C. solution of 4-methyl-2-[3-(1-methyl-piperidin-4-yl)-propylamino]-pyrimidine-5-carboxylic acid ethyl ester (0.20 g, 0.63 mmol) in THF (6 mL) was added diisobutylaluminum hydride (1 M in hexanes; 1.25 mL, 1.25 mmol) dropwise. The mixture was warmed to rt over 1 h. The reaction was quenched with 1 M H$_2$SO$_4$ (2 mL). The mixture was neutralized with satd. aq. NaHCO$_3$, and diluted with MeOH (2 mL), CHCl$_3$ (10 mL), and satd. aq. sodium potassium tartrate (10 mL). The mixture was stirred vigourously until the layers separated. The organic layer was dried (Na$_2$SO$_4$) and concentrated to give the crude product (138 mg), which was used in the next step without further purification. $^1$H NMR (CDCl$_3$): 8.07 (s, 1H), 4.52 (s, 2H), 3.42-3.33 (m, 2H), 2.88-2.74 (m, 2H), 2.41 (s, 3H), 2.23 (s, 3H), 1.93-1.83 (m, 2H), 1.72-1.53 (m, 4H), 1.35-1.16 (m, 5H).

Step E; [5-(5-Fluoro-4-methyl-1H-benzoimidazol-2-yl)-pyrimidin-2-yl]-[3-(1-methyl-piperidin-4-yl)-propyl]-amine A mixture of 4-methyl-2-[3-(1-methyl-piperidin-4-yl)-propylamino]-pyrimidin-5-yl}-methanol (0.14 g, 0.49 mmol) in toluene (3 mL) was added MnO$_2$ (0.22 g, 2.48 mmol). After 30 min at 70° C., the mixture was filtered through diatomaceous earth. The filtrate was concentrated and immediately dissolved in DMF. A portion of this solution (corresponding to 0.05 mg, 0.17 mmol of 4-methyl-2-[3-(1-methyl-piperidin-4-yl)-propylamino]-pyrimidine-5-carbaldehyde) was then treated with 4-fluoro-3-methyl-benzene-1,2-diamine (1.1 equiv.) and Na$_2$H$_2$S$_2$O$_5$ (1.25 equiv.) at 90° C. for 12 h. The reaction mixture was purified by FCC to afford the title compound. MS: mass calcd. for C$_{22}$H$_{29}$FN$_6$, 396.24; m/z found, 397.2 [M+H]$^+$. $^1$H NMR (CD$_3$OD): 8.62 (s, 1H), 7.55 (dd, J=8.0, 3.9 Hz, 1H), 7.17 (dd, J=10.3, 8.8 Hz, 1H), 3.60 (t, J=6.9 Hz, 2H), 3.10-2.99 (m, 2H), 2.71 (s, 3H), 2.66 (d, J=1.4 Hz, 3H), 2.44 (s, 3H), 2.26-2.17 (m, 2H), 1.98-1.88 (m, 2H), 1.87-1.77 (m, 2H), 1.55-1.36 (m, 5H).

The following compounds in Examples 2-14 were synthesized analogously to the procedures described in Example 1.

Example 2

[5-(4,6-Dimethyl-1H-benzoimidazol-2-yl)-4-methyl-pyrimidin-2-yl]-[3-(1-methyl-piperidin-4-yl)-propyl]-amine

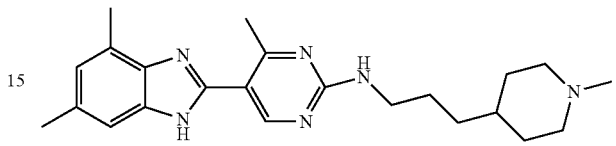

MS: mass calcd. for C$_{23}$H$_{32}$N$_6$, 392.27; m/z found, 393.3 [M+H]$^+$. $^1$H NMR (CD$_3$OD): 8.43 (s, 1H), 7.20 (s, 1H), 6.89 (s, 1H), 3.41 (t, J=7.0 Hz, 2H), 2.89-2.82 (m, 2H), 2.54 (s, 3H), 2.53 (s, 3H), 2.42 (s, 3H), 2.25 (s, 3H), 2.05-1.96 (m, 2H), 1.78-1.70 (m, 2H), 1.69-1.59 (m, 2H), 1.34-1.21 (m, 5H).

Example 3

[5-(6-Fluoro-4-methyl-1H-benzoimidazol-2-yl)-4-methyl-pyrimidin-2-yl]-[3-(1-methyl-piperidin-4-yl)-propyl]-amine

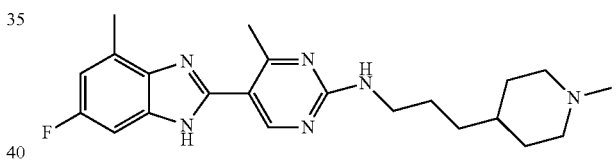

MS: mass calcd. for C$_{22}$H$_{29}$FN$_6$, 396.24; m/z found, 397.3 [M+H]$^+$. $^1$H NMR (CD$_3$OD): 8.45 (s, 1H), 7.10 (dd, J=8.9, 2.1 Hz, 1H), 6.85 (dd, J=10.5, 1.5 Hz, 1H), 3.42 (t, J=7.0 Hz, 2H), 2.90-2.82 (m, 2H), 2.58 (s, 3H), 2.54 (s, 3H), 2.25 (s, 3H), 2.05-1.93 (m, 2H), 1.78-1.71 (m, 2H), 1.69-1.60 (m, 2H), 1.39-1.18 (m, 5H).

Example 4

[5-(4,5-Difluoro-1H-benzoimidazol-2-yl)-4-methyl-pyrimidin-2-yl]-[3-(1-methyl-piperidin-4-yl)-propyl]-amine

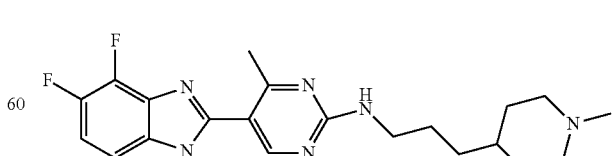

MS: mass calcd. for C$_{21}$H$_{26}$F$_2$N$_6$, 400.22; m/z found, 401.2 [M+H]$^+$. $^1$H NMR (CD$_3$OD): 8.49 (s, 1H), 7.32 (ddd, J=8.8, 3.7, 1.1 Hz, 1H), 7.17 (ddd, J=11.4, 8.8, 7.2 Hz, 1H), 3.43 (t, J=7.0 Hz, 2H), 2.93-2.82 (m, 2H), 2.58 (s, 3H), 2.27 (s, 3H), 2.08-1.97 (m, 2H), 1.79-1.71 (m, 2H), 1.70-1.60 (m, 2H), 1.40-1.16 (m, 5H).

Example 5

[5-(4,5-Dimethyl-1H-benzoimidazol-2-yl)-4-methyl-pyrimidin-2-yl]-[3-(1-methyl-piperidin-4-yl)-propyl]-amine

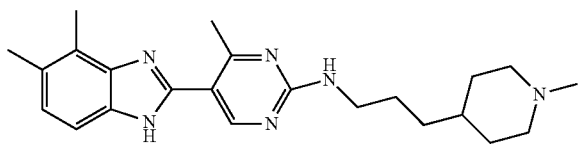

MS: mass calcd. for $C_{23}H_{32}N_6$, 392.27; m/z found, 393.3 [M+H]$^+$. $^1$H NMR (CD$_3$OD): 8.44 (s, 1H), 7.31 (d, J=7.7 Hz, 1H), 7.07 (d, J=8.2 Hz, 1H), 3.43 (t, J=7.3 Hz, 1H), 2.92-2.82 (m, 2H), 2.53 (s, 3H), 2.51 (s, 3H), 2.39 (s, 3H), 2.26 (s, 3H), 2.07-1.96 (m, 2H), 1.79-1.71 (m, 2H), 1.71-1.61 (m, 2H), 1.41-1.16 (m, 5H).

Example 6

[5-(4,6-Difluoro-1H-benzoimidazol-2-yl)-4-methyl-pyrimidin-2-yl]-[3-(1-methyl-piperidin-4-yl)-propyl]-amine

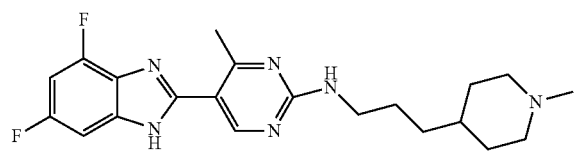

MS: mass calcd. for $C_{21}H_{26}F_2N_6$, 400.22; m/z found, 401.2 [M+H]$^+$. $^1$H NMR (CD$_3$OD): 8.48 (s, 1H), 7.13 (dd, J=8.5, 2.1 Hz, 1H), 6.88 (dt, J=10.4, 10.4, 2.2 Hz, 1H), 3.42 (t, J=6.9 Hz, 2H), 2.91-2.82 (m, 2H), 2.57 (s, 3H), 2.26 (s, 3H), 2.07-1.97 (m, 2H), 1.80-1.71 (m, 2H), 1.70-1.59 (m, 2H), 1.40-1.17 (m, 5H).

Example 7

[5-(4,6-Dimethyl-1H-benzoimidazol-2-yl)-4-methyl-pyrimidin-2-yl]-methyl-[3-(1-methyl-piperidin-4-yl)-propyl]-amine

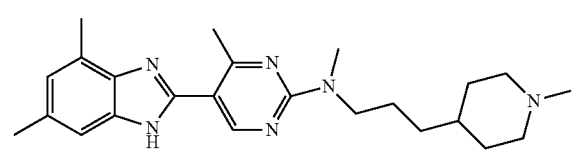

MS: mass calcd. for $C_{24}H_{34}N_6$, 406.28; m/z found, 407.3 [M+H]$^+$. $^1$H NMR (CD$_3$OD): 8.31 (s, 1H), 7.04 (s, 1H), 6.73 (s, 1H), 3.55 (t, J=7.3 Hz, 2H), 3.04 (s, 3H), 2.75-2.67 (m, 2H), 2.39 (s, 6H), 2.26 (s, 3H), 2.10 (s, 3H), 1.90-1.82 (m, 2H), 1.63-1.47 (m, 4H), 1.17-1.01 (m, 5H).

Example 8

[5-(4,5-Dimethyl-1H-benzoimidazol-2-yl)-4-ethyl-pyrimidin-2-yl]-methyl-[3-(1-methyl-piperidin-4-yl)-propyl]-amine

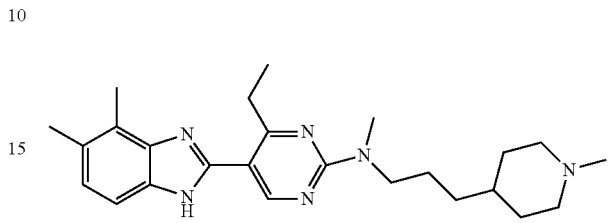

MS: mass calcd. for $C_{24}H_{34}N_6$, 406.28; m/z found, 407.3 [M+H]$^+$. $^1$H NMR (CD$_3$OD): 8.37 (s, 1H), 7.31 (d, J=8.1 Hz, 1H), 7.06 (d, J=8.2 Hz, 1H), 3.43 (t, J=6.2 Hz, 2H), 2.94-2.81 (m, 4H), 2.50 (s, 3H), 2.39 (s, 3H), 2.25 (s, 3H), 2.05-1.95 (m, 2H), 1.79-1.70 (m, 2H), 1.71-1.61 (m, 2H), 1.40-1.10 (m, 8H).

Example 9

[5-(4,5-Difluoro-1H-benzoimidazol-2-yl)-4-ethyl-pyrimidin-2-yl]-[3-(1-methyl-piperidin-4-yl)-propyl]-amine

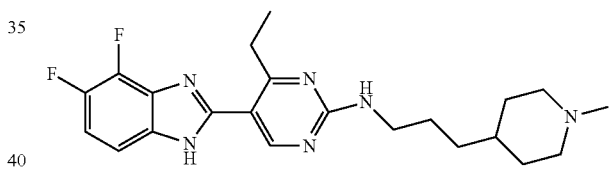

MS: mass calcd. for $C_{22}H_{28}F_2N_6$, 414.23; m/z found, 415.3 [M+H]$^+$. $^1$H NMR (CD$_3$OD): 8.42 (s, 1H), 7.32 (ddd, J=8.8, 3.6, 1.2 Hz, 1H), 7.17 (ddd, J=11.4, 8.8, 7.2 Hz, 1H), 3.48-3.39 (m, 2H), 3.01-2.91 (m, 2H), 2.90-2.83 (m, 2H), 2.26 (s, 3H), 2.07-1.96 (m, 2H), 1.79-1.60 (m, 4H), 1.38-1.11 (m, 8H).

Example 10

[5-(4-Fluoro-5-methyl-1H-benzoimidazol-2-yl)-4-propyl-pyrimidin-2-yl]-[3-(1-methyl-piperidin-4-yl)-propyl]-amine

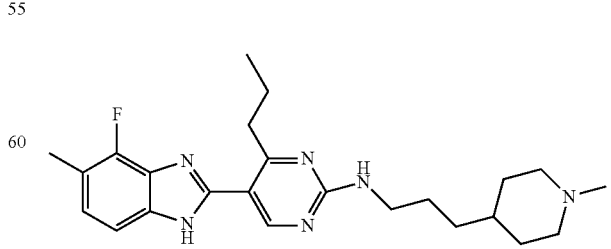

MS: mass calcd. for $C_{24}H_{33}FN_6$, 424.28; m/z found, 425.3 [M+H]$^+$. $^1$H NMR (CD$_3$OD): 8.39 (s, 1H), 7.37 (dd, J=8.5, 4.2 Hz, 1H), 7.00 (dd, J=10.3, 8.9 Hz, 1H), 3.43 (t, J=6.4 Hz, 2H), 2.91-2.82 (m, 4H), 2.49 (d, J=1.4 Hz, 3H), 2.25 (s, 3H), 2.05-1.96 (m, 2H), 1.81-1.57 (m, 6H), 1.40-1.16 (m, 5H), 0.90-0.83 (m, 3H).

Example 11

[5-(4,5-Dimethyl-1H-benzoimidazol-2-yl)-4-isopropyl-pyrimidin-2-yl]-[3-(1-methyl-piperidin-4-yl)-propyl]-amine

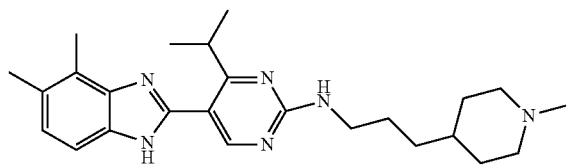

MS: mass calcd. for $C_{25}H_{36}N_6$, 420.30; m/z found, 421.3 [M+H]$^+$. $^1$H NMR (CD$_3$OD): 8.30 (s, 1H), 7.31 (d, J=8.1 Hz, 1H), 7.07 (d, J=8.2 Hz, 1H), 3.47-3.38 (m, 3H), 2.94-2.73 (m, 2H), 2.50 (s, 3H), 2.39 (s, 3H), 2.25 (s, 3H), 2.05-1.91 (m, 2H), 1.80-1.60 (m, 4H), 1.40-1.21 (m, 5H), 1.19 (d, J=6.7 Hz, 6H).

Example 12

[5-(4,6-Dimethyl-1H-benzoimidazol-2-yl)-4-isopropyl-pyrimidin-2-yl]-[3-(1-methyl-piperidin-4-yl)-propyl]-amine

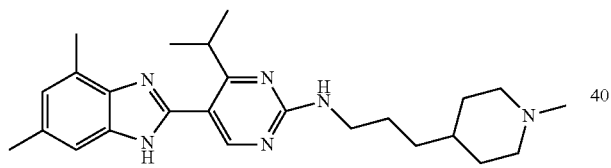

MS: mass calcd. for $C_{25}H_{36}N_6$, 420.30; m/z found, 421.3 [M+H]$^+$. $^1$H NMR (CD$_3$OD): 8.29 (s, 1H), 7.19 (s, 1H), 6.90 (s, 1H), 3.50-3.37 (m, 3H), 3.07-2.97 (m, 2H), 2.54 (s, 3H), 2.43 (s, 3H), 2.40 (s, 3H), 2.30-2.20 (m, 2H), 1.85-1.78 (m, 2H), 1.73-1.64 (m, 2H), 1.42-1.26 (m, 5H), 1.19 (d, J=6.7 Hz, 6H).

Example 13

[4-Cyclobutyl-5-(4,5-dimethyl-1H-benzoimidazol-2-yl)-pyrimidin-2-yl]-[3-(1-methyl-piperidin-4-yl)-propyl]-amine

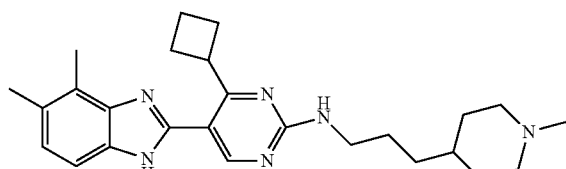

MS: mass calcd. for $C_{26}H_{36}N_6$, 432.30; m/z found, 433.3 [M+H]$^+$. $^1$H NMR (CD$_3$OD): 8.31 (s, 1H), 7.31 (d, J=7.7 Hz, 1H), 7.06 (d, J=8.2 Hz, 1H), 4.02 (p, J=8.4 Hz, 1H), 3.57-3.38 (m, 2H), 2.93-2.81 (m, 2H), 2.50 (s, 3H), 2.39 (s, 3H), 2.38-2.32 (m, 2H), 2.26 (s, 3H), 2.14-1.86 (m, 5H), 1.87-1.61 (m, 5H), 1.43-1.18 (m, 5H).

Example 14

[4-Cyclobutyl-5-(4,5-difluoro-1H-benzoimidazol-2-yl)-pyrimidin-2-yl]-[3-(1-methyl-piperidin-4-yl)-propyl]-amine

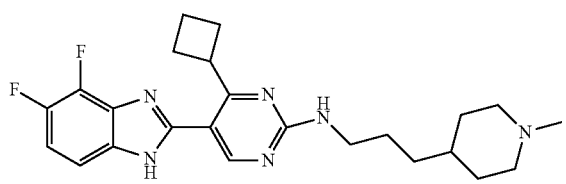

MS: mass calcd. for $C_{24}H_{30}F_2N_6$, 440.25; m/z found, 441.3 [M+H]$^+$. $^1$H NMR (CD$_3$OD): 8.36 (s, 1H), 7.32 (ddd, J=8.8, 3.6, 1.1 Hz, 1H), 7.17 (ddd, J=11.4, 8.8, 7.2 Hz, 1H), 4.10 (p, J=8.4 Hz, 1H), 3.57-3.39 (m, 2H), 2.92-2.81 (m, 2H), 2.42-2.29 (m, 2H), 2.27-2.24 (m, 3H), 2.19-2.06 (m, 2H), 2.06-1.94 (m, 2H), 1.90-1.60 (m, 6H), 1.40-1.14 (m, 5H).

Example 15

[5-(5-Fluoro-4-methyl-1H-benzoimidazol-2-yl)-pyrimidin-2-yl]-[3-(1-methyl-piperidin-4-yl)-propyl]-amine

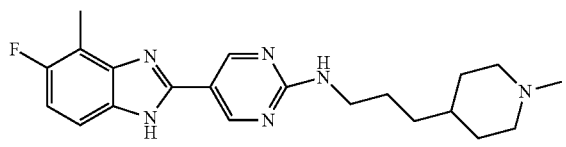

The title compound was prepared from 2-methylsulfanyl-pyrimidine-5-carboxylic acid methyl ester (Zhichkin, P. et al., Synthesis 2002, 6, 720-722) using methods analogous to those described in Example 1. MS: mass calcd. for $C_{21}H_{27}FN_6$, 382.23; m/z found, 383.4 [M+H]$^+$. $^1$H NMR (CD$_3$OD): 9.02-8.85 (m, 2H), 7.45-7.27 (m, 1H), 6.98 (dd, J=10.1, 8.9 Hz, 1H), 3.43 (t, J=7.1 Hz, 2H), 2.96-2.88 (m, 2H), 2.51 (s, 3H), 2.30 (s, 3H), 2.14-2.03 (m, 2H), 1.83-1.72 (m, 2H), 1.72-1.61 (m, 2H), 1.41-1.18 (m, 5H).

The compounds in Examples 16-32 were prepared using methods analogous to those described in Example 1.

Example 16

[4-Cyclobutyl-5-(5-fluoro-4-methyl-1H-benzoimidazol-2-yl)-pyrimidin-2-yl]-[3-(1-methyl-piperidin-4-yl)-propyl]-amine

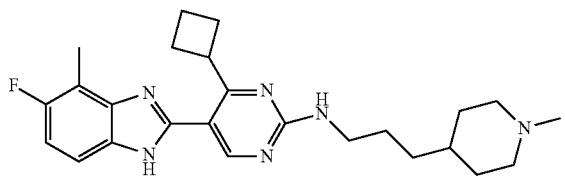

MS: mass calcd. for $C_{25}H_{33}FN_6$, 436.28; m/z found, 437.3 [M+H]$^+$.

Example 17

[4-Cyclobutyl-5-(4,6-dimethyl-1H-benzoimidazol-2-yl)-pyrimidin-2-yl]-[3-(1-methyl-piperidin-4-yl)-propyl]-amine

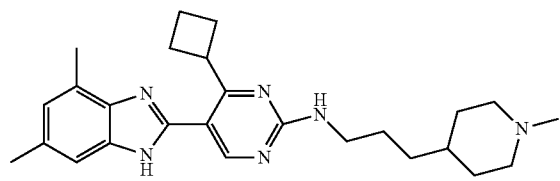

MS: mass calcd. for $C_{26}H_{36}N_6$, 432.30; m/z found, 433.3 [M+H]$^+$.

Example 18

[5-(4,5-Dimethyl-1H-benzoimidazol-2-yl)-4-propyl-pyrimidin-2-yl]-[3-(1-methyl-piperidin-4-yl)-propyl]-amine

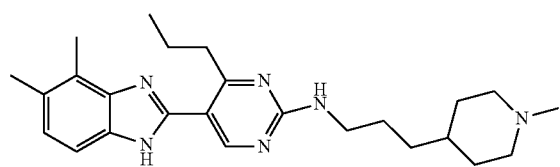

MS: mass calcd. for $C_{25}H_{36}N_6$, 420.30; m/z found, 421.3 [M+H]$^+$.

Example 19

[4-Ethyl-5-(5-fluoro-4-methyl-1H-benzoimidazol-2-yl)-pyrimidin-2-yl]-[3-(1-methyl-piperidin-4-yl)-propyl]-amine

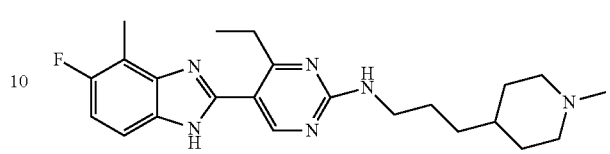

MS: mass calcd. for $C_{23}H_{31}FN_6$, 410.26; m/z found, 411.3 [M+H]$^+$.

Example 20

[5-(5-Fluoro-4-methyl-1H-benzoimidazol-2-yl)-4-isopropyl-pyrimidin-2-yl]-[3-(1-methyl-piperidin-4-yl)-propyl]-amine

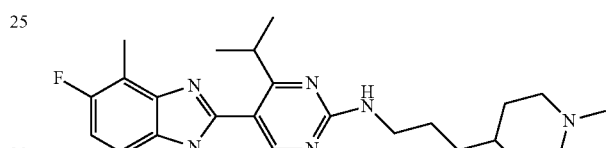

MS: mass calcd. for $C_{24}H_{33}FN_6$, 424.28; m/z found, 425.3 [M+H]$^+$.

Example 21

[4-Methyl-5-(4-methyl-1H-benzoimidazol-2-yl)-pyrimidin-2-yl]-[3-(1-methyl-piperidin-4-yl)-propyl]-amine

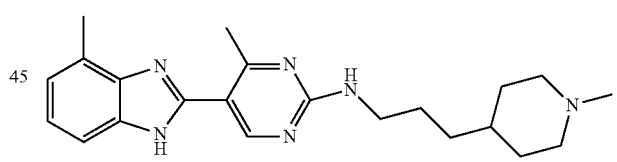

MS: mass calcd. for $C_{22}H_{30}N_6$, 378.25; m/z found, 379.3 [M+H]$^+$.

Example 22

[5-(1H-Benzoimidazol-2-yl)-4-methyl-pyrimidin-2-yl]-[3-(1-methyl-piperidin-4-yl)-propyl]-amine

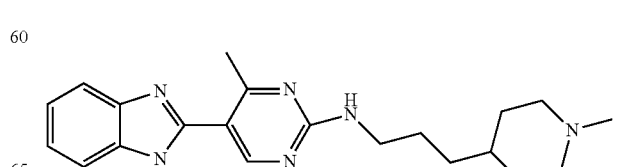

MS: mass calcd. for $C_{21}H_{28}N_6$, 364.24; m/z found, 365.2 [M+H]$^+$.

Example 23

[5-(5-Fluoro-1H-benzoimidazol-2-yl)-4-methyl-pyrimidin-2-yl]-[3-(1-methyl-piperidin-4-yl)-propyl]-amine

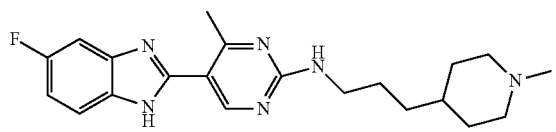

MS: mass calcd. for $C_{21}H_{27}FN_6$, 382.23; m/z found, 383.2 [M+H]$^+$.

Example 24

[3-(1-Methyl-piperidin-4-yl)-propyl]-[4-methyl-5-(5-trifluoromethyl-1H-benzoimidazol-2-yl)-pyrimidin-2-yl]-amine

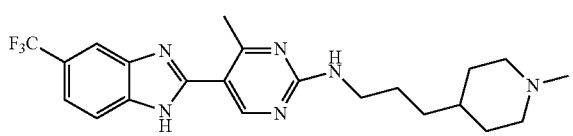

MS: mass calcd. for $C_{22}H_{27}F_3N_6$, 432.22; m/z found, 433.2 [M+H]$^+$.

Example 25

[5-(5-tert-Butyl-1H-benzoimidazol-2-yl)-4-methyl-pyrimidin-2-yl]-[3-(1-methyl-piperidin-4-yl)-propyl]-amine

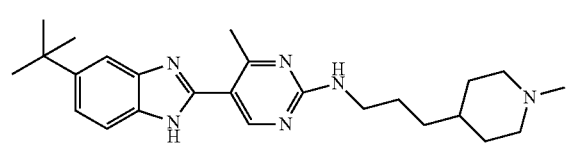

MS: mass calcd. for $C_{25}H_{36}N_6$, 420.30; m/z found, 421.3 [M+H]$^+$.

Example 26

[5-(5-Chloro-4-methyl-1H-benzoimidazol-2-yl)-4-methyl-pyrimidin-2-yl]-[3-(1-methyl-piperidin-4-yl)-propyl]-amine

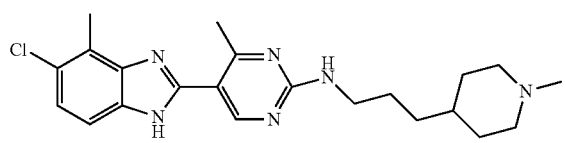

MS: mass calcd. for $C_{22}H_{29}ClN_6$, 412.21; m/z found, 413.2 [M+H]$^+$.

Example 27

[5-(5-Fluoro-4-methyl-1H-benzoimidazol-2-yl)-4-trifluoromethyl-pyrimidin-2-yl]-[3-(1-methyl-piperidin-4-yl)-propyl]-amine MS: mass calcd. for $C_{22}H_{26}F_4N_6$, 450.22; m/z found, 451.2 [M+H]$^+$.

Example 28

[5-(6-Fluoro-4-methyl-1H-benzoimidazol-2-yl)-4-trifluoromethyl-pyrimidin-2-yl]-[3-(1-methyl-piperidin-4-yl)-propyl]-amine

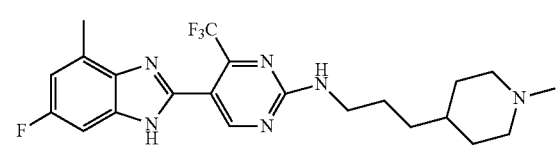

MS: mass calcd. for $C_{22}H_{26}F_4N_6$, 450.22; m/z found, 451.2 $[M+H]^+$.

Example 29

[5-(4,6-Dichloro-1H-benzoimidazol-2-yl)-4-trifluoromethyl-pyrimidin-2-yl]-[3-(1-methyl-piperidin-4-yl)-propyl]-amine

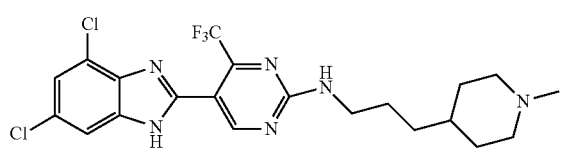

MS: mass calcd. for $C_{21}H_{23}Cl_2F_3N_6$, 486.13; m/z found, 487.1 $[M+H]^+$.

Example 30

[5-(4,5-Dimethyl-1H-benzoimidazol-2-yl)-4-trifluoromethyl-pyrimidin-2-yl]-[3-(1-methyl-piperidin-4-yl)-propyl]-amine

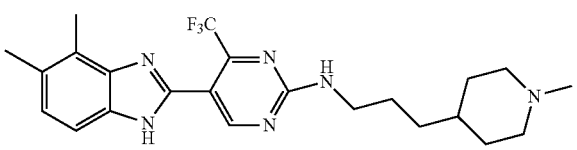

MS: mass calcd. for $C_{23}H_{29}F_3N_6$, 446.24; m/z found, 447.3 $[M+H]^+$.

Example 31

[5-(5,6-Difluoro-1H-benzoimidazol-2-yl)-4-trifluoromethyl-pyrimidin-2-yl]-[3-(1-methyl-piperidin-4-yl)-propyl]-amine

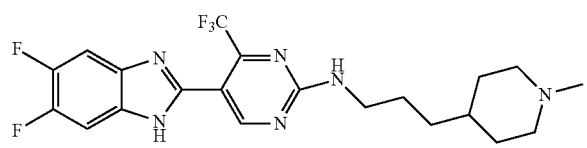

MS: mass calcd. for $C_{21}H_{23}F_5N_6$, 454.19; m/z found, 455.2 $[M+H]^+$.

Example 32

[5-(4,5-Difluoro-1H-benzoimidazol-2-yl)-4-isopropyl-pyrimidin-2-yl]-[3-(1-methyl-piperidin-4-yl)-propyl]-amine

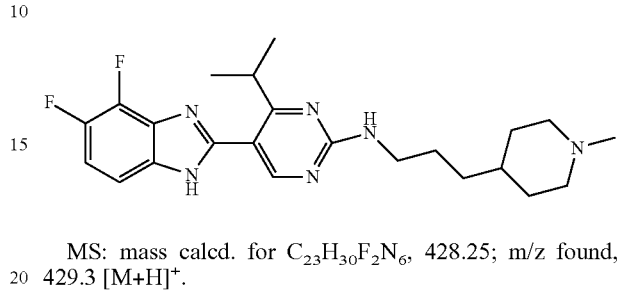

MS: mass calcd. for $C_{23}H_{30}F_2N_6$, 428.25; m/z found, 429.3 $[M+H]^+$.

Example 33

[5-(5-Fluoro-4-methyl-1H-benzoimidazol-2-yl)-pyrazin-2-yl]-[3-(1-methyl-piperidin-4-yl)-propyl]-amine

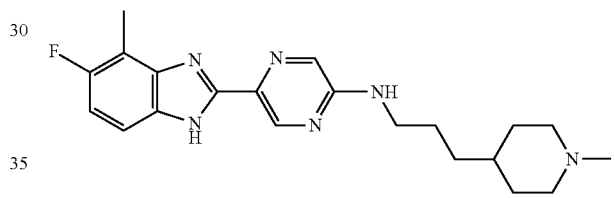

Step A; 5-[3-(1-Methyl-piperidin-4-yl)-propylamino]-pyrazine-2-carboxylic acid methyl ester A solution of 5-chloro-pyrazine-2-carboxylic acid methyl ester (1 equiv.) and 3-(1-methyl-piperidin-4-yl)-propylamine (1.1 equiv.) in MeOH (0.25 M) heated at 100° C. in a sealed tube for 4 h. The mixture was cooled to rt and concentrated to give a crude product which was purified by FCC.

Step B; 5-[3-(1-Methyl-piperidin-4-yl)-propylamino]-pyrazine-2-carbaldehyde

A −78° C. solution of 5-[3-(1-methyl-piperidin-4-yl)-propylamino]-pyrazine-2-carboxylic acid methyl ester in DCM (0.1 M) was treated with diisobutylaluminum hydride (1 M in hexanes; 1 equiv.) dropwise. The reaction was quenched with 1 M $H_2SO_4$, neutralized with satd. aq. $NaHCO_3$, and diluted with MeOH, $CHCl_3$, and satd. aq. sodium potassium tartrate. The mixture was stirred vigourously until the layers separated. The organic layer was dried ($Na_2SO_4$) and concentrated to give the crude product, which was used in the next step without further purification.

Step C

The title compound was prepared using methods analogous to those described in Example 1, Step E, Part 2, to provide the title compound. MS: mass calcd. for $C_{21}H_{27}FN_6$, 382.23; m/z found, 383.2 $[M+H]^+$.

Example 34

[5-(4,5-Dimethyl-1H-benzoimidazol-2-yl)-pyrazin-2-yl]-[3-(1-methyl-piperidin-4-yl)-propyl]-amine

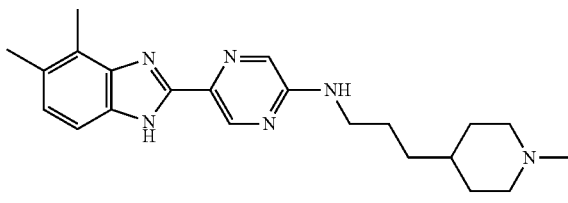

The title compound was prepared using methods analogous to those described in Example 33. MS: mass calcd. for $C_{22}H_{30}N_6$, 378.25; m/z found, 379.3 [M+H]$^+$.

The compounds in Examples 35-50 were prepared using methods analogous to those described in the preceding examples.

Example 35

[5-(4,6-Bis-trifluoromethyl-1H-benzoimidazol-2-yl)-4-methyl-pyrimidin-2-yl]-[3-(1-methyl-piperidin-4-yl)-propyl]-amine

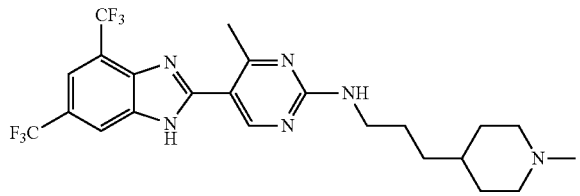

MS (ESI): mass calcd. for $C_{23}H_{26}F_6N_6$, 500.49; m/z found, 501.2 [M+H]$^+$.

Example 36

2-{4-Methyl-2-[3-(1-methyl-piperidin-4-yl)-propylamino]-pyrimidin-5-yl}-1H-benzoimidazole-5-carbonitrile

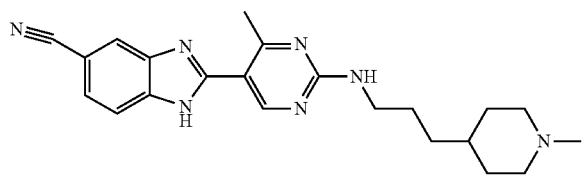

MS (ESI): mass calcd. for $C_{22}H_{27}N_7$, 389.51; m/z found, 390.3 [M+H]$^+$. $^1$H NMR (MeOD): 8.55 (s, 1H), 7.99 (dd, J=1.3, 0.5 Hz, 1H), 7.72 (dd, J=8.3, 0.5 Hz, 1H), 7.57 (dd, J=8.4, 1.5 Hz, 1H), 3.43 (t, J=6.8 Hz, 2H), 2.89 (d, J=12.1 Hz, 2H), 2.62 (s, 3H), 2.28 (s, 3H), 2.05 (t, J=11.8 Hz, 2H), 1.76 (d, J=11.3 Hz, 2H), 1.66 (td, J=14.7, 7.5 Hz, 2H), 1.30 (m, 5H).

Example 37

[5-(5-Methoxy-1H-benzoimidazol-2-yl)-4-methyl-pyrimidin-2-yl]-[3-(1-methyl-piperidin-4-yl)-propyl]-amine

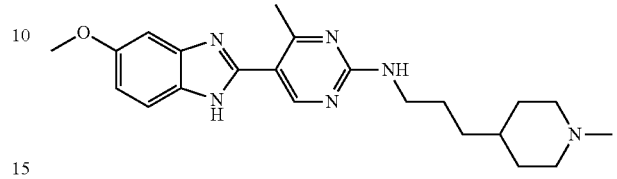

MS (ESI): mass calcd. for $C_{22}H_{30}N_6O$, 394.52; m/z found, 395.3 [M+H]$^+$. $^1$H NMR (MeOD): 8.45 (s, 1H), 7.46 (s, J=8.8 Hz, 1H), 6.90 (dd, J=8.8, 2.4 Hz, 1H), 7.09 (s, 1H), 3.85 (s, 3H), 3.42 (t, J=7.1 Hz, 2H), 2.88 (d, J=11.9 Hz, 2H), 2.56 (s, 3H), 2.27 (s, 3H), 2.03 (t, J=11.7 Hz, 2H), 1.75 (d, J=12.7 Hz, 2H), 1.66 (td, J=15.0, 7.6 Hz, 2H), 1.38-1.20 (m, 5H).

Example 38

[5-(4-Chloro-6-trifluoromethyl-1H-benzoimidazol-2-yl)-4-methyl-pyrimidin-2-yl]-[3-(1-methyl-piperidin-4-yl)-propyl]-amine

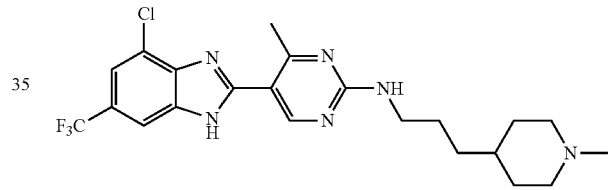

MS (ESI): mass calcd. for $C_{22}H_{26}ClF_3N_6$, 466.94; m/z found, 467.2 [M+H]$^+$. $^1$H NMR (MeOD): 8.55 (s, 1H), 7.83 (s, 1H), 7.55-7.53 (m, 1H), 3.43 (t, J=6.9 Hz, 2H), 2.88 (d, J=11.9 Hz, 2H), 2.61 (s, 3H), 2.27 (s, 3H), 2.04 (t, J=11.8 Hz, 2H), 1.75 (d, J=12.0 Hz, 2H), 1.66 (m, 2H), 1.38-1.18 (m, 5H).

Example 39

[5-(5-Chloro-6-fluoro-1H-benzoimidazol-2-yl)-4-methyl-pyrimidin-2-yl]-[3-(1-methyl-piperidin-4-yl)-propyl]-amine

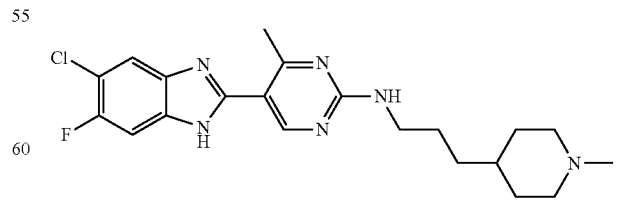

MS (ESI): mass calcd. for $C_{21}H_{26}ClFN_6$, 416.93; m/z found, 417.2 [M+H]$^+$. $^1$H NMR (MeOD): 8.49 (s, 1H), 7.67 (d, J=6.6 Hz, 1H), 7.44 (d, J=9.3 Hz, 1H), 3.42 (t, J=7.0 Hz, 2H), 2.87 (d, J=11.9 Hz, 2H), 2.58 (s, 3H), 2.25 (s, 3H), 2.01

(t, J=12.7 Hz, 2H), 1.74 (d, J=12.1 Hz, 2H), 1.65 (dd, J=14.8, 7.2 Hz, 2H), 1.41-1.16 (m, 5H).

Example 40

[5-(5-Chloro-1H-benzoimidazol-2-yl)-4-methyl-pyrimidin-2-yl]-[3-(1-methyl-piperidin-4-yl)-propyl]-amine

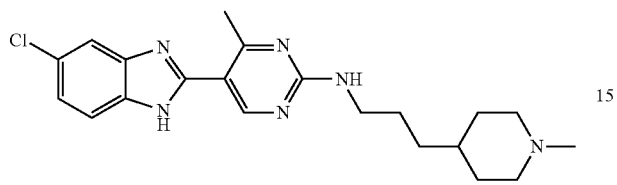

MS (ESI): mass calcd. for $C_{21}H_{27}ClN_6$, 398.94; m/z found, 399.2 [M+H]$^+$. $^1$H NMR (MeOD): 8.49 (s, 1H), 7.59 (d, J=1.8 Hz, 1H), 7.55 (d, J=8.6 Hz, 1H), 7.25 (dd, J=8.6, 2.0 Hz, 1H), 3.42 (t, J=6.9 Hz, 2H), 2.87 (d, J=12.0 Hz, 2H), 2.58 (s, 3H), 2.26 (s, 3H), 2.02 (t, J=11.7 Hz, 2H), 1.75 (d, J=12.1 Hz, 2H), 1.65 (td, J=14.8, 7.4 Hz, 2H), 1.38-1.19 (m, 5H).

Example 41

[5-(5,6-Dichloro-1H-benzoimidazol-2-yl)-4-methyl-pyrimidin-2-yl]-[3-(1-methyl-piperidin-4-yl)-propyl]-amine

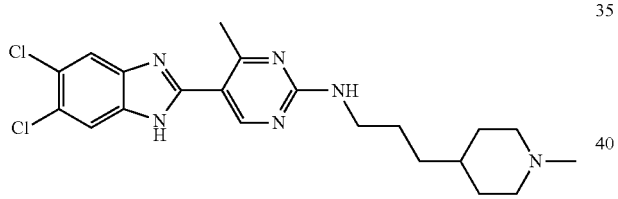

MS (ESI): mass calcd. for $C_{21}H_{26}Cl_2N_6$, 433.39; m/z found, 433.2 [M+H]$^+$. $^1$H NMR (MeOD): 8.50 (s, 1H), 7.74 (s, 2H), 3.43 (t, J=7.1 Hz, 2H), 2.93 (d, J=11.6 Hz, 2H), 2.59 (s, 3H), 2.31 (s, 3H), 2.11 (t, J=11.3 Hz, 2H), 1.78 (d, J=12.4 Hz, 2H), 1.66 (m, 2H), 1.33 (m, 6H).

Example 42

[5-(4,6-Dimethyl-1H-benzoimidazol-2-yl)-4-ethyl-pyrimidin-2-yl]-[3-(1-methyl-piperidin-4-yl)-propyl]-amine

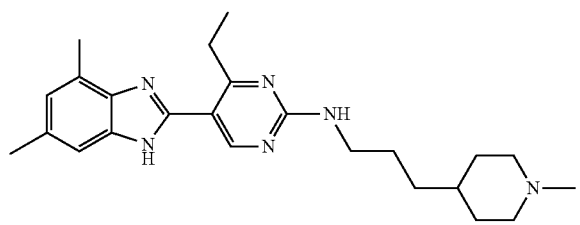

MS (ESI): mass calcd. for $C_{24}H_{34}N_6$, 406.58; m/z found, 407.3 [M+H]$^+$. $^1$H NMR (MeOD): 8.36 (s, 1H), 7.19 (s, 1H), 6.89 (s, 1H), 3.46-3.39 (m, 2H), 2.88 (dd, J=15.1, 7.8 Hz, 4H), 2.54 (s, 3H), 2.42 (s, 3H), 2.26 (s, 3H), 2.01 (t, J=10.9 Hz, 2H), 1.74 (d, J=11.9 Hz, 2H), 1.66 (dd, J=14.4, 7.2 Hz, 2H), 1.26 (m, 8H).

Example 43

[4-Ethyl-5-(4-methyl-1H-benzoimidazol-2-yl)-pyrimidin-2-yl]-[3-(1-methyl-piperidin-4-yl)-propyl]-amine

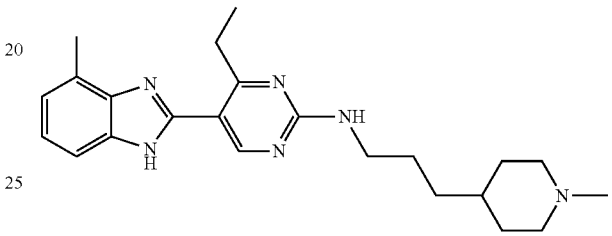

MS (ESI): mass calcd. for $C_{23}H_{32}N_6$, 392.55; m/z found, 393.3 [M+H]$^+$. $^1$H NMR (MeOD): 8.39 (s, 1H), 7.41 (d, J=7.7 Hz, 1H), 7.15 (t, J=7.7 Hz, 1H), 7.05 (d, J=7.3 Hz, 1H), 3.44 (t, J=5.2 Hz, 2H), 2.89 (s, 4H), 2.58 (s, 3H), 2.27 (s, 3H), 2.03 (t, J=11.7 Hz, 2H), 1.75 (d, J=12.4 Hz, 2H), 1.67 (td, J=14.9, 7.3 Hz, 2H), 1.41-1.12 (m, 8H).

Example 44

[4-Cyclopropyl-5-(4-methyl-1H-benzoimidazol-2-yl)-pyrimidin-2-yl]-[3-(1-methyl-piperidin-4-yl)-propyl]-amine

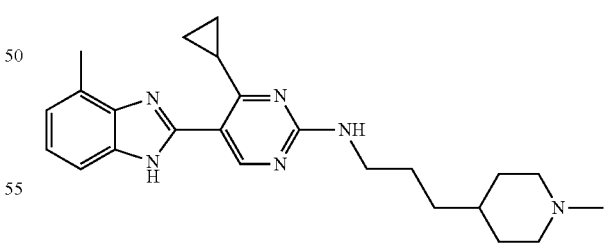

MS (ESI): mass calcd. for $C_{24}H_{32}N_6$, 404.56; m/z found, 405.3 [M+H]$^+$. $^1$H NMR (MeOD): 8.32 (s, 1H), 7.41 (d, J=6.5 Hz, 1H), 7.17-7.12 (m, 1H), 7.05 (d, J=7.3 Hz, 1H), 3.39-3.34 (m, 2H), 2.89 (d, J=12.0 Hz, 2H), 2.59 (s, 3H), 2.47 (s, 1H), 2.28 (s, 3H), 2.05 (t, J=11.6 Hz, 2H), 1.75 (d, J=12.0 Hz, 2H), 1.67-1.58 (m, 2H), 1.38-1.17 (m, 7H), 1.02 (dd, J=7.3, 3.0 Hz, 2H).

Example 45

[4-Cyclopropyl-5-(4,5-dimethyl-1H-benzoimidazol-2-yl)-pyrimidin-2-yl]-[3-(1-methyl-piperidin-4-yl)-propyl]-amine

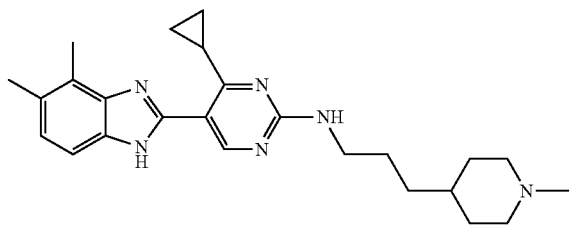

MS (ESI): mass calcd. for $C_{25}H_{34}N_6$, 418.59; m/z found, 419.3 [M+H]$^+$. $^1$H NMR (MeOD): 8.31 (s, 1H), 7.31 (d, J=7.2 Hz, 1H), 7.06 (d, J=8.2 Hz, 1H), 3.36 (t, J=7.1 Hz, 2H), 2.88 (d, J=12.0 Hz, 2H), 2.56-2.42 (m, 4H), 2.39 (s, 3H), 2.27 (s, 3H), 2.03 (t, J=11.6 Hz, 2H), 1.74 (d, J=11.7 Hz, 2H), 1.62 (td, J=14.7, 7.5 Hz, 2H), 1.38-1.16 (m, 7H), 1.01 (dd, J=7.5, 3.1 Hz, 2H).

Example 46

[4-Cyclopropyl-5-(6-fluoro-4-methyl-1H-benzoimidazol-2-yl)-pyrimidin-2-yl]-[3-(1-methyl-piperidin-4-yl)-propyl]-amine

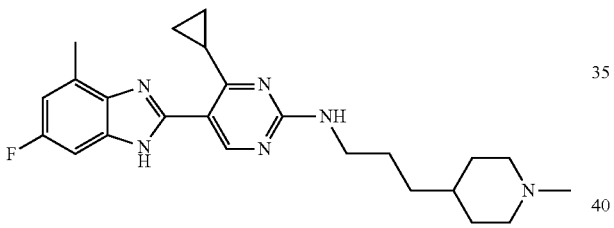

MS (ESI): mass calcd. for $C_{24}H_{31}FN_6$, 422.55; m/z found, 423.3 [M+H]$^+$. $^1$H NMR (MeOD): 8.32 (s, 1H), 7.10 (d, J=8.0 Hz, 1H), 6.86 (dd, J=10.5, 1.5 Hz, 1H), 3.36 (t, J=7.3 Hz, 2H), 2.91 (d, J=12.1 Hz, 2H), 2.59 (s, 3H), 2.48 (s, 1H), 2.29 (s, 3H), 2.07 (t, J=10.8 Hz, 2H), 1.76 (d, J=12.3 Hz, 2H), 1.62 (dd, J=14.3, 7.4 Hz, 2H), 1.40-1.17 (m, 7H), 1.05-0.98 (m, 2H).

Example 47

[4-Cyclopropyl-5-(4,6-dimethyl-1H-benzoimidazol-2-yl)-pyrimidin-2-yl]-[3-(1-methyl-piperidin-4-yl)-propyl]-amine

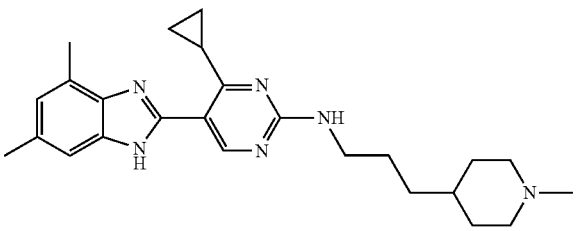

MS (ESI): mass calcd. for $C_{25}H_{34}N_6$, 418.59; m/z found, 419.3 [M+H]$^+$. $^1$H NMR (MeOD): 8.30 (s, 1H), 7.20 (s, 1H), 6.89 (s, 1H), 3.36 (t, J=7.0 Hz, 2H), 2.88 (d, J=11.5 Hz, 2H), 2.54 (s, 3H), 2.46 (s, 1H), 2.42 (s, 3H), 2.27 (s, 3H), 2.03 (t, J=11.0 Hz, 2H), 1.74 (d, J=11.4 Hz, 2H), 1.66-1.57 (m, 2H), 1.38-1.16 (m, 7H), 1.04-0.98 (m, 2H).

Example 48

[4-Cyclopropyl-5-(5-fluoro-4-methyl-1H-benzoimidazol-2-yl)-pyrimidin-2-yl]-[3-(1-methyl-piperidin-4-yl)-propyl]-amine

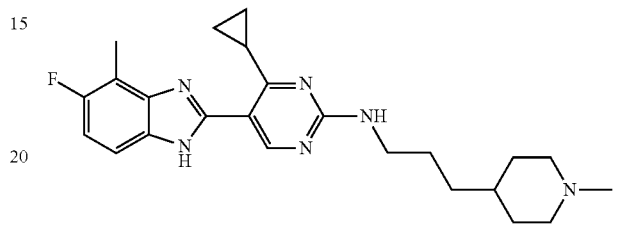

MS (ESI): mass calcd. for $C_{24}H_{31}FN_6$, 422.55; m/z found, 423.3 [M+H]$^+$. $^1$H NMR (MeOD): 8.33 (s, 1H), 7.38 (s, 1H), 7.01 (dd, J=10.3, 8.8 Hz, 1H), 3.37 (t, J=7.0 Hz, 1H), 2.91 (d, J=11.9 Hz, 2H), 2.54-2.43 (m, 4H), 2.30 (s, 3H), 2.08 (t, J=10.9 Hz, 2H), 1.94 (s, 1H), 1.76 (d, J=12.4 Hz, 2H), 1.68-1.59 (m, 2H), 1.42-1.17 (m, 7H), 1.06-1.00 (m, 2H).

The compounds in Examples 49-50 are prepared using methods analogous to those described in the preceding examples.

Example 49

[5-(6-Chloro-5-methyl-1H-benzoimidazol-2-yl)-4-methyl-pyrimidin-2-yl]-[3-(1-methyl-piperidin-4-yl)-propyl]-amine

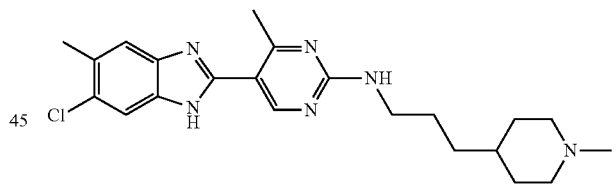

Example 50

[5-(4-Chloro-6-methyl-1H-benzoimidazol-2-yl)-4-methyl-pyrimidin-2-yl]-[3-(1-methyl-piperidin-4-yl)-propyl]-amine

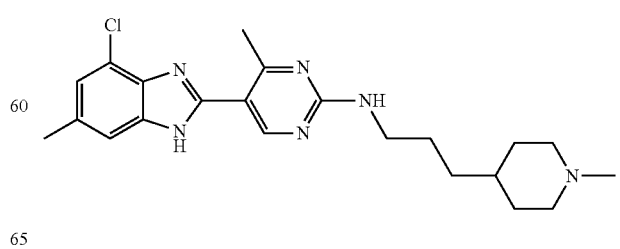

Additional examples of embodiments of this invention are provided by hemitartrate salts of compounds of Formula (I)

and by hydrates, such as monohydrates and dihydrates, of compounds of Formula (I). For example, embodiments of this invention include hydrates, such as monohydrates and dihydrates of, and/or hemitartrate salts of compounds selected from the group consisting of:

[5-(5-Fluoro-4-methyl-1H-benzoimidazol-2-yl)-4-methyl-pyrimidin-2-yl]-[3-(1-methyl-piperidin-4-yl)-propyl]-amine;

[5-(4,6-Dimethyl-1H-benzoimidazol-2-yl)-4-methyl-pyrimidin-2-yl]-[3-(1-methyl-piperidin-4-yl)-propyl]-amine;

[5-(6-Fluoro-4-methyl-1H-benzoimidazol-2-yl)-4-methyl-pyrimidin-2-yl]-[3-(1-methyl-piperidin-4-yl)-propyl]-amine;

[5-(4,5-Difluoro-1H-benzoimidazol-2-yl)-4-methyl-pyrimidin-2-yl]-[3-(1-methyl-piperidin-4-yl)-propyl]-amine;

[5-(4,5-Dimethyl-1H-benzoimidazol-2-yl)-4-methyl-pyrimidin-2-yl]-[3-(1-methyl-piperidin-4-yl)-propyl]-amine;

[5-(4,6-Difluoro-1H-benzoimidazol-2-yl)-4-methyl-pyrimidin-2-yl]-[3-(1-methyl-piperidin-4-yl)-propyl]-amine;

[5-(4,6-Dimethyl-1H-benzoimidazol-2-yl)-4-methyl-pyrimidin-2-yl]-methyl-[3-(1-methyl-piperidin-4-yl)-propyl]-amine;

[5-(4,5-Dimethyl-1H-benzoimidazol-2-yl)-4-ethyl-pyrimidin-2-yl]-methyl-[3-(1-methyl-piperidin-4-yl)-propyl]-amine;

[5-(4,5-Difluoro-1H-benzoimidazol-2-yl)-4-ethyl-pyrimidin-2-yl]-[3-(1-methyl-piperidin-4-yl)-propyl]-amine;

[5-(4-Fluoro-5-methyl-1H-benzoimidazol-2-yl)-4-propyl-pyrimidin-2-yl]-[3-(1-methyl-piperidin-4-yl)-propyl]-amine;

[5-(4,5-Dimethyl-1H-benzoimidazol-2-yl)-4-isopropyl-pyrimidin-2-yl]-[3-(1-methyl-piperidin-4-yl)-propyl]-amine;

[5-(4,6-Dimethyl-1H-benzoimidazol-2-yl)-4-isopropyl-pyrimidin-2-yl]-[3-(1-methyl-piperidin-4-yl)-propyl]-amine;

[4-Cyclobutyl-5-(4,5-dimethyl-1H-benzoimidazol-2-yl)-pyrimidin-2-yl]-[3-(1-methyl-piperidin-4-yl)-propyl]-amine;

[4-Cyclobutyl-5-(4,5-difluoro-1H-benzoimidazol-2-yl)-pyrimidin-2-yl]-[3-(1-methyl-piperidin-4-yl)-propyl]-amine;

[5-(5-Fluoro-4-methyl-1H-benzoimidazol-2-yl)-pyrimidin-2-yl]-[3-(1-methyl-piperidin-4-yl)-propyl]-amine;

[4-Cyclobutyl-5-(5-fluoro-4-methyl-1H-benzoimidazol-2-yl)-pyrimidin-2-yl]-[3-(1-methyl-piperidin-4-yl)-propyl]-amine;

[4-Cyclobutyl-5-(4,6-dimethyl-1H-benzoimidazol-2-yl)-pyrimidin-2-yl]-[3-(1-methyl-piperidin-4-yl)-propyl]-amine;

[5-(4,5-Dimethyl-1H-benzoimidazol-2-yl)-4-propyl-pyrimidin-2-yl]-[3-(1-methyl-piperidin-4-yl)-propyl]-amine;

[4-Ethyl-5-(5-fluoro-4-methyl-1H-benzoimidazol-2-yl)-pyrimidin-2-yl]-[3-(1-methyl-piperidin-4-yl)-propyl]-amine;

[5-(5-Fluoro-4-methyl-1H-benzoimidazol-2-yl)-4-isopropyl-pyrimidin-2-yl]-[3-(1-methyl-piperidin-4-yl)-propyl]-amine;

[4-Methyl-5-(4-methyl-1H-benzoimidazol-2-yl)-pyrimidin-2-yl]-[3-(1-methyl-piperidin-4-yl)-propyl]-amine;

[5-(1H-Benzoimidazol-2-yl)-4-methyl-pyrimidin-2-yl]-[3-(1-methyl-piperidin-4-yl)-propyl]-amine;

[5-(5-Fluoro-1H-benzoimidazol-2-yl)-4-methyl-pyrimidin-2-yl]-[3-(1-methyl-piperidin-4-yl)-propyl]-amine;

[3-(1-Methyl-piperidin-4-yl)-propyl]-[4-methyl-5-(5-trifluoromethyl-1H-benzoimidazol-2-yl)-pyrimidin-2-yl]-amine;

[5-(5-tert-Butyl-1H-benzoimidazol-2-yl)-4-methyl-pyrimidin-2-yl]-[3-(1-methyl-piperidin-4-yl)-propyl]-amine;

[5-(5-Chloro-4-methyl-1H-benzoimidazol-2-yl)-4-methyl-pyrimidin-2-yl]-[3-(1-methyl-piperidin-4-yl)-propyl]-amine;

[5-(5-Fluoro-4-methyl-1H-benzoimidazol-2-yl)-4-trifluoromethyl-pyrimidin-2-yl]-[3-(1-methyl-piperidin-4-yl)-propyl]-amine;

[5-(6-Fluoro-4-methyl-1H-benzoimidazol-2-yl)-4-trifluoromethyl-pyrimidin-2-yl]-[3-(1-methyl-piperidin-4-yl)-propyl]-amine;

[5-(4,6-Dichloro-1H-benzoimidazol-2-yl)-4-trifluoromethyl-pyrimidin-2-yl]-[3-(1-methyl-piperidin-4-yl)-propyl]-amine;

[5-(4,5-Dimethyl-1H-benzoimidazol-2-yl)-4-trifluoromethyl-pyrimidin-2-yl]-[3-(1-methyl-piperidin-4-yl)-propyl]-amine;

[5-(5,6-Difluoro-1H-benzoimidazol-2-yl)-4-trifluoromethyl-pyrimidin-2-yl]-[3-(1-methyl-piperidin-4-yl)-propyl]-amine;

[5-(4,5-Difluoro-1H-benzoimidazol-2-yl)-4-isopropyl-pyrimidin-2-yl]-[3-(1-methyl-piperidin-4-yl)-propyl]-amine;

[5-(1H-Benzoimidazol-2-yl)-pyrazin-2-yl]-[3-(1-methyl-piperidin-4-yl)-propyl]-amine;

[5-(4,5-Dimethyl-1H-benzoimidazol-2-yl)-pyrazin-2-yl]-[3-(1-methyl-piperidin-4-yl)-propyl]-amine;

[5-(4,6-Bis-trifluoromethyl-1H-benzoimidazol-2-yl)-4-methyl-pyrimidin-2-yl]-[3-(1-methyl-piperidin-4-yl)-propyl]-amine;

2-{4-Methyl-2-[3-(1-methyl-piperidin-4-yl)-propylamino]-pyrimidin-5-yl}-1H-benzoimidazole-5-carbonitrile;

[5-(5-Methoxy-1H-benzoimidazol-2-yl)-4-methyl-pyrimidin-2-yl]-[3-(1-methyl-piperidin-4-yl)-propyl]-amine;

[5-(4-Chloro-6-trifluoromethyl-1H-benzoimidazol-2-yl)-4-methyl-pyrimidin-2-yl]-[3-(1-methyl-piperidin-4-yl)-propyl]-amine;

[5-(5-Chloro-6-fluoro-1H-benzoimidazol-2-yl)-4-methyl-pyrimidin-2-yl]-[3-(1-methyl-piperidin-4-yl)-propyl]-amine;

[5-(5-Chloro-1H-benzoimidazol-2-yl)-4-methyl-pyrimidin-2-yl]-[3-(1-methyl-piperidin-4-yl)-propyl]-amine;

[5-(5,6-Dichloro-1H-benzoimidazol-2-yl)-4-methyl-pyrimidin-2-yl]-[3-(1-methyl-piperidin-4-yl)-propyl]-amine;

[5-(4,6-Dimethyl-1H-benzoimidazol-2-yl)-4-ethyl-pyrimidin-2-yl]-[3-(1-methyl-piperidin-4-yl)-propyl]-amine;

[4-Ethyl-5-(4-methyl-1H-benzoimidazol-2-yl)-pyrimidin-2-yl]-[3-(1-methyl-piperidin-4-yl)-propyl]-amine;

[4-Cyclopropyl-5-(4-methyl-1H-benzoimidazol-2-yl)-pyrimidin-2-yl]-[3-(1-methyl-piperidin-4-yl)-propyl]-amine;

[4-Cyclopropyl-5-(4,5-dimethyl-1H-benzoimidazol-2-yl)-pyrimidin-2-yl]-[3-(1-methyl-piperidin-4-yl)-propyl]-amine;

[4-Cyclopropyl-5-(6-fluoro-4-methyl-1H-benzoimidazol-2-yl)-pyrimidin-2-yl]-[3-(1-methyl-piperidin-4-yl)-propyl]-amine;

[4-Cyclopropyl-5-(4,6-dimethyl-1H-benzoimidazol-2-yl)-pyrimidin-2-yl]-[3-(1-methyl-piperidin-4-yl)-propyl]-amine;

[4-Cyclopropyl-5-(5-fluoro-4-methyl-1H-benzoimidazol-2-yl)-pyrimidin-2-yl]-[3-(1-methyl-piperidin-4-yl)-propyl]-amine;

[5-(6-Chloro-5-methyl-1H-benzoimidazol-2-yl)-4-methyl-pyrimidin-2-yl]-[3-(1-methyl-piperidin-4-yl)-propyl]-amine; and

[5-(4-Chloro-6-methyl-1H-benzoimidazol-2-yl)-4-methyl-pyrimidin-2-yl]-[3-(1-methyl-piperidin-4-yl)-propyl]-amine.

Biological Testing:
Binding Assay on Recombinant Human Histamine $H_4$ Receptor

SK-N-MC cells or COS7 cells were transiently transfected with pH4R and grown in 150 $cm^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 sec at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10,000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK-N-MC or COS7 cells expressing human histamine $H_4$ receptor were used to measure the affinity of binding of other compounds and their ability to displace $^3$H-ligand binding by incubating the above-described reaction in the presence of various concentrations of inhibitor or compound to be tested. For competition binding studies using $^3$H-histamine, $K_i$ values were calculated, based on an experimentally determined $K_D$ value of 5 nM and a ligand concentration of 5 nM, according to Y.-C. Cheng and W. H. Prusoff (*Biochem. Pharmacol.* 1973, 22(23):3099-3108): $K_i=(IC_{50})/(1+([L]/(K_D))$. Results for the compounds tested in this assay are presented in Table 1 as an average of results obtained, and rounded to the nearest 10 nM.

TABLE 1

| EX | $K_i$ (nM) |
| --- | --- |
| 1 | 21 |
| 2 | 11 |
| 3 | 4 |
| 4 | 11 |
| 5 | 4 |
| 6 | 17 |
| 7 | 83 |
| 8 | 29 |
| 9 | 210 |
| 10 | 470 |
| 11 | 360 |
| 12 | 200 |
| 13 | 430 |
| 14 | 1010 |
| 15 | 290 |
| 16 | 1470 |
| 17 | 1320 |
| 18 | 2410 |
| 19 | NT |
| 20 | 230 |
| 21 | 27 |
| 22 | 110 |
| 23 | 59 |
| 24 | 12 |
| 25 | 13 |
| 26 | 13 |
| 27 | 92 |
| 28 | 62 |
| 29 | 35 |
| 30 | 230 |
| 31 | 230 |
| 32 | 6110 |
| 33 | 250 |
| 34 | 680 |
| 35 | 11 |
| 36 | 170 |
| 37 | 81 |

TABLE 1-continued

| EX | $K_i$ (nM) |
| --- | --- |
| 38 | 2 |
| 39 | 15 |
| 40 | 7 |
| 41 | 6 |
| 42 | 22 |
| 43 | 110 |
| 44 | 560 |
| 45 | 390 |
| 46 | 230 |
| 47 | 99 |
| 48 | 140 |

While the invention has been illustrated by reference to examples, it is understood that the invention is intended not to be limited to the foregoing detailed description.

What is claimed is:
1. A chemical entity selected from:
[5-(6-Fluoro-4-methyl-1H-benzoimidazol-2-yl)-4-methyl-pyrimidin-2-yl]-[3-(1-methyl-piperidin-4-yl)-propyl]-amine;
[5-(4,6-Difluoro-1H-benzoimidazol-2-yl)-4-methyl-pyrimidin-2-yl]-[3-(1-methyl-piperidin-4-yl)-propyl]-amine;
[5-(4,6-Dimethyl-1H-benzoimidazol-2-yl)-4-methyl-pyrimidin-2-yl]-methyl-[3-(1-methyl-piperidin-4-yl)-propyl]-amine;
[5-(4,6-Dimethyl-1H-benzoimidazol-2-yl)-4-isopropyl-pyrimidin-2-yl]-[3-(1-methyl-piperidin-4-yl)-propyl]-amine;
[4-Cyclobutyl-5-(4,6-dimethyl-1H-benzoimidazol-2-yl)-pyrimidin-2-yl]-[3-(1-methyl-piperidin-4-yl)-propyl]-amine;
[5-(6-Fluoro-4-methyl-1H-benzoimidazol-2-yl)-4-trifluoromethyl-pyrimidin-2-yl]-[3-(1-methyl-piperidin-4-yl)-propyl]-amine;
[5-(4,6-Bis-trifluoromethyl-1H-benzoimidazol-2-yl)-4-methyl-pyrimidin-2-yl]-[3-(1-methyl-piperidin-4-yl)-propyl]-amine;
[5-(4-Chloro-6-trifluoromethyl-1H-benzoimidazol-2-yl)-4-methyl-pyrimidin-2-yl]-[3-(1-methyl-piperidin-4-yl)-propyl]-amine;
[5-(4,6-Dimethyl-1H-benzoimidazol-2-yl)-4-ethyl-pyrimidin-2-yl]-[3-(1-methyl-piperidin-4-yl)-propyl]-amine;
[4-Cyclopropyl-5-(6-fluoro-4-methyl-1H-benzoimidazol-2-yl)-pyrimidin-2-yl]-[3-(1-methyl-piperidin-4-yl)-propyl]-amine;
[4-Cyclopropyl-5-(4,6-dimethyl-1H-benzoimidazol-2-yl)-pyrimidin-2-yl]-[3-(1-methyl-piperidin-4-yl)-propyl]-amine;
[5-(4-Chloro-6-methyl-1H-benzoimidazol-2-yl)-4-methyl-pyrimidin-2-yl]-[3-(1-methyl-piperidin-4-yl)-propyl]-amine;
and pharmaceutically acceptable salts thereof.
2. A pharmaceutical composition comprising a pharmaceutically acceptable excipient and an effective amount of a compound selected from:
[5-(6-Fluoro-4-methyl-1H-benzoimidazol-2-yl)-4-methyl-pyrimidin-2-yl]-[3-(1-methyl-piperidin-4-yl)-propyl]-amine;
[5-(4,6-Difluoro-1H-benzoimidazol-2-yl)-4-methyl-pyrimidin-2-yl]-[3-(1-methyl-piperidin-4-yl)-propyl]-amine;

[5-(4,6-Dimethyl-1H-benzoimidazol-2-yl)-4-methyl-pyrimidin-2-yl]-methyl-[3-(1-methyl-piperidin-4-yl)-propyl]-amine;

[5-(4,6-Dimethyl-1H-benzoimidazol-2-yl)-4-isopropyl-pyrimidin-2-yl]-[3-(1-methyl-piperidin-4-yl)-propyl]-amine;

[4-Cyclobutyl-5-(4,6-dimethyl-1H-benzoimidazol-2-yl)-pyrimidin-2-yl]-[3-(1-methyl-piperidin-4-yl)-propyl]-amine;

[5-(6-Fluoro-4-methyl-1H-benzoimidazol-2-yl)-4-trifluoromethyl-pyrimidin-2-yl]-[3-(1-methyl-piperidin-4-yl)-propyl]-amine;

[5-(4,6-Bis-trifluoromethyl-1H-benzoimidazol-2-yl)-4-methyl-pyrimidin-2-yl]-[3-(1-methyl-piperidin-4-yl)-propyl]-amine;

[5-(4-Chloro-6-trifluoromethyl-1H-benzoimidazol-2-yl)-4-methyl-pyrimidin-2-yl]-[3-(1-methyl-piperidin-4-yl)-propyl]-amine;

[5-(4,6-Dimethyl-1H-benzoimidazol-2-yl)-4-ethyl-pyrimidin-2-yl]-[3-(1-methyl-piperidin-4-yl)-propyl]-amine;

[4-Cyclopropyl-5-(6-fluoro-4-methyl-1H-benzoimidazol-2-yl)-pyrimidin-2-yl]-[3-(1-methyl-piperidin-4-yl)-propyl]-amine;

[4-Cyclopropyl-5-(4,6-dimethyl-1H-benzoimidazol-2-yl)-pyrimidin-2-yl]-[3-(1-methyl-piperidin-4-yl)-propyl]-amine;

[5-(4-Chloro-6-methyl-1H-benzoimidazol-2-yl)-4-methyl-pyrimidin-2-yl]-[3-(1-methyl-piperidin-4-yl)-propyl]-amine;

and pharmaceutically acceptable salts thereof.

* * * * *